Figure 1:
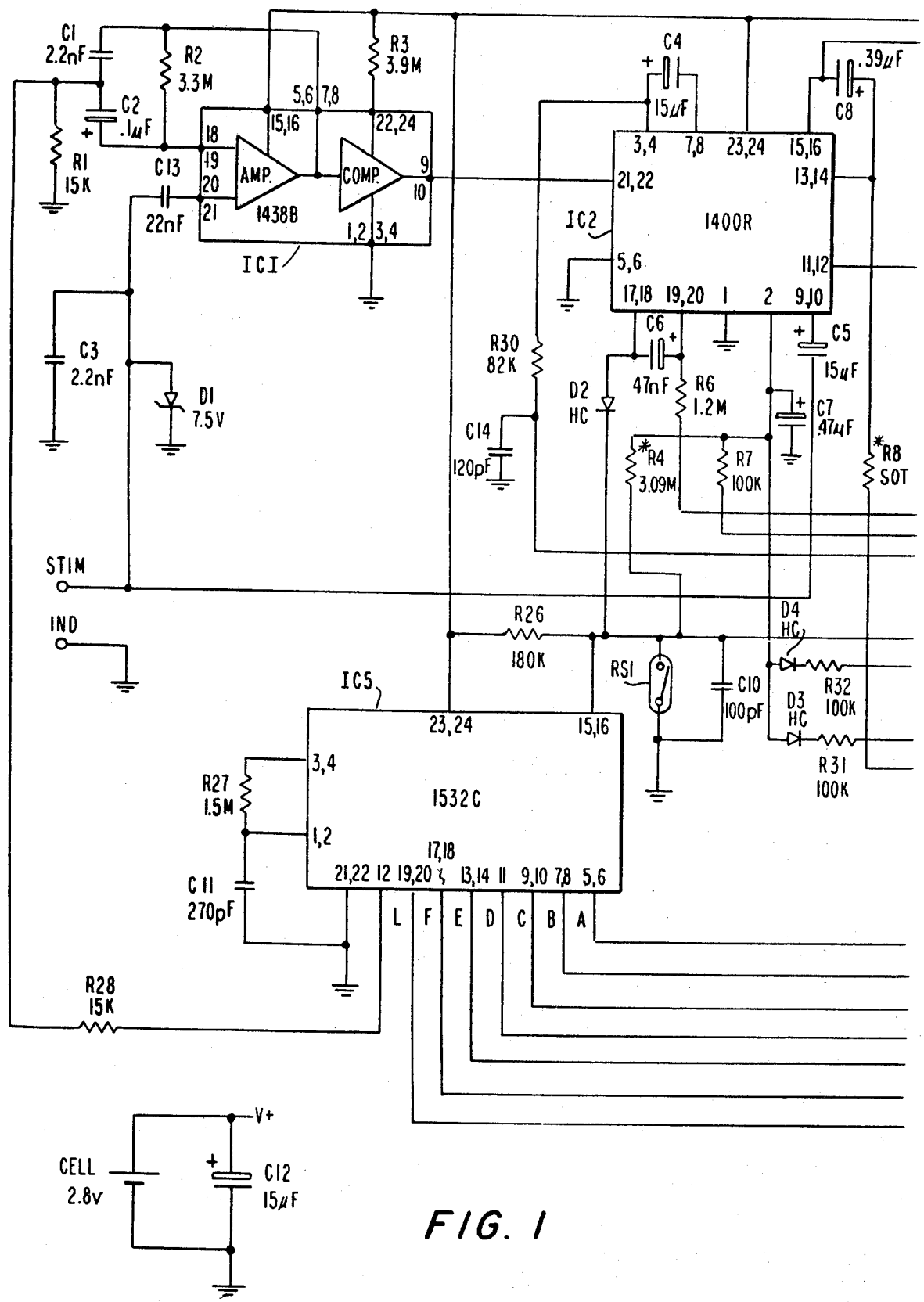

United States Patent [19]

Nappholz et al.

[11] 4,398,536

[45] Aug. 16, 1983

[54] SCANNING BURST TACHYCARDIA CONTROL PACER

[75] Inventors: Tibor A. Nappholz, Drummoyne; Stephen J. Swift, Hornsby, both of Australia

[73] Assignee: Telectronics Pty. Ltd., Lane Cove, Australia

[21] Appl. No.: 284,349

[22] Filed: Jul. 17, 1981

[51] Int. Cl.³ .................................. A61N 1/36
[52] U.S. Cl. .................................. 128/419 PG
[58] Field of Search ........ 128/419 P, 419 PG, 419 D, 128/702, 703, 705, 706, 795, 796

[56] References Cited

U.S. PATENT DOCUMENTS

| | | | |
|---|---|---|---|
| 3,693,627 | 9/1972 | Berkovits | 128/419 PG |
| 3,698,398 | 10/1972 | Berkovits | 128/419 PG |
| 3,939,844 | 2/1976 | Pequignot | 128/419 PG |
| 3,942,534 | 3/1976 | Allen et al. | 128/419 PG |
| 4,163,451 | 8/1979 | Lesnik et al. | 128/419 PG |
| 4,181,133 | 1/1980 | Kolenik et al. | 128/419 PG |
| 4,280,502 | 7/1981 | Baker, Jr. et al. | 128/419 PG |
| 4,307,725 | 12/1981 | Sowton et al. | 128/419 PG |
| 4,312,356 | 1/1982 | Sowton et al. | 128/419 PG |

Primary Examiner—William E. Kamm
Assistant Examiner—Mitchell J. Shein
Attorney, Agent, or Firm—Gottlieb, Rackman and Reisman

[57] ABSTRACT

There is disclosed an improved pacer for controlling tachycardia. Following each tachycardia confirmation, a burst of a programmed number (e.g., 15) of stimulating pulses is generated. The rates of the bursts increase from cycle to cycle; thus following each tachycardia confirmation, a pulse burst at a different rate is generated. The rate of a burst which is successful in terminating tachycardia is stored, and following the next tachycardia confirmation the stored rate is used for the first burst which is generated. In this manner, there is a greater likelihood that tachycardia will be terminated following the first burst since a previously successful rate is used. Only if success is not achieved does scanning of the burst rate ensue, starting with the previously successful rate.

54 Claims, 12 Drawing Figures

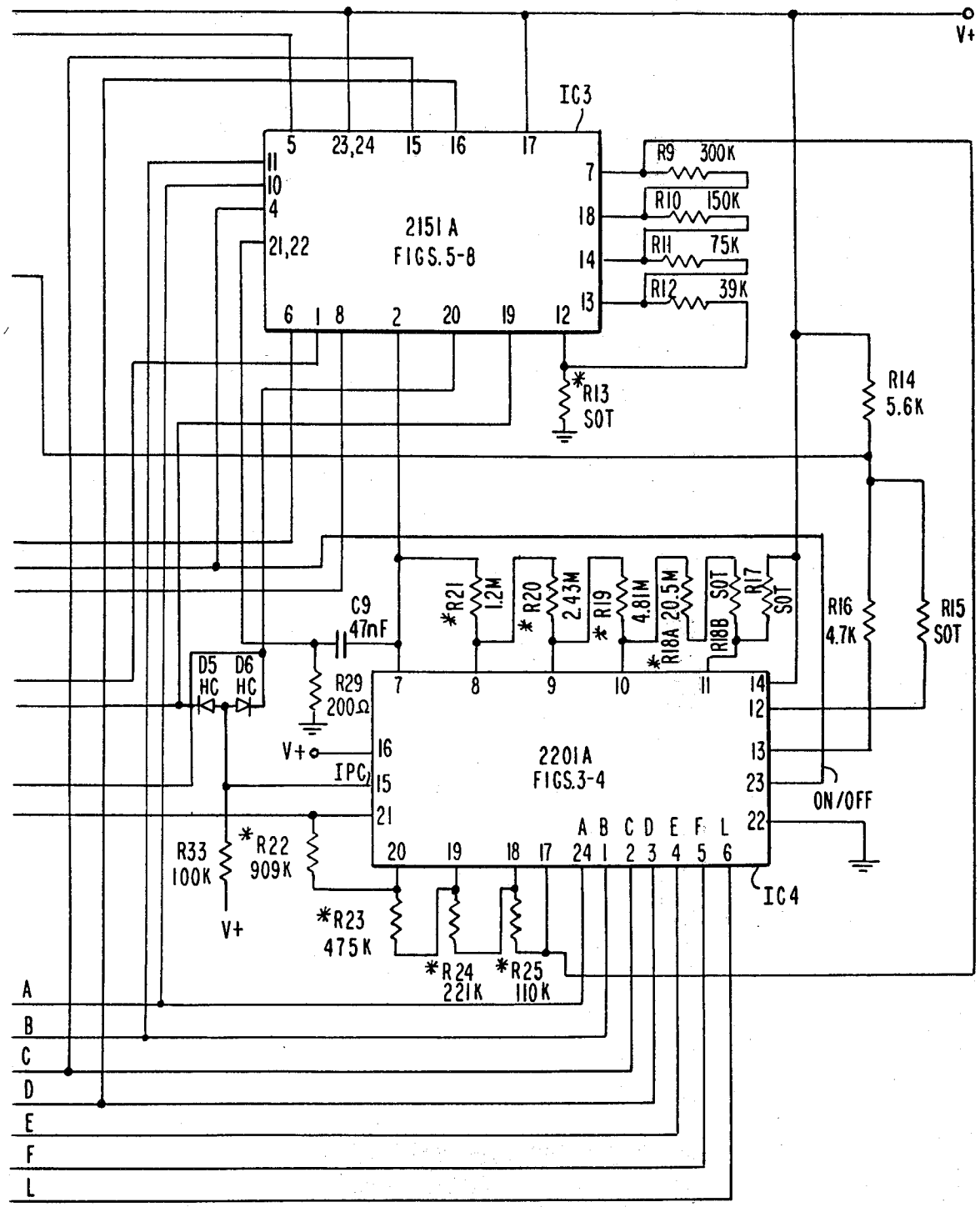
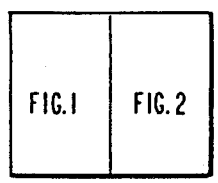
FIG. 2
FIG. 2A

SCANNING BURST TACHYCARDIA CONTROL PACER

DESCRIPTION

This invention relates to tachycardia control pacers, and more particularly to such pacers which generate stimulating pulse bursts.

Tachycardia is a condition in which the heart beats very rapidly, typically, above 150 beats per minute. There are several different pacing modalities which have been suggested for termination of tachycardia. The underlying principle in all of them is that if a pacer stimulates the heart at least once shortly after a heartbeat, before the next naturally occurring heartbeat at the rapid rate, the heart may successively revert to sinus rhythm. Tachycardia is often the result of electrical feedback within the heart; a natural beat results in the feedback of an electrical stimulus which prematurely triggers another beat. By interposing a stimulated heartbeat, the stability of the feedback loop is disrupted. As with conventional heart pacers, the electrodes of a tachycardia control pacer may be atrially-coupled or ventricularly-coupled. Although the detection of atrial beats and atrial stimulation are preferred, ventricular beat detection and pacing may also be employed.

In the copending application of Spurrell et al, entitled "Two-Pulse Tachycardia Control Pacer", Ser. No. 245,215, filed on Mar. 19, 1981, which application is hereby incorporated by reference, there is disclosed a tachycardia control pacer which generates a single stimulus, or two stimuli, following each confirmation of tachycardia. The delay between the last heartbeat which is used to confirm a tachycardia episode and the first stimulus is referred to as the "initial delay", and the interval between the first stimulus and the second (if a second stimulus is generated) is referred to as the "coupled interval". In the Spurrell et al pacer, the physician may program maximum values for the initial delay and the coupled interval. The pacer automatically scans both the initial delay and the coupled interval during successive cycles, both scanning sequences involving fifteen 6-millisecond decrements. The net result is that up to 256 different timed pairs of stimuli may be generated in an effort to terminate tachycardia.

The difficulty in tachycardia control is that there is usually no way of knowing exactly when a stimulating pulse should be applied. One or more pulses should be applied shortly after a heartbeat and prior to the time when the next premature beat would otherwise occur, but there is usually no way of knowing precisely when the pulses should be generated. As an alternative to the Spurrell et al type of control, it has been proposed to generate a single pulse after the last heartbeat in the tachycardia confirmation cycle which is related to the heartbeat rate. By keying the single pulse which is generated to the actual rate at which the heart is beating, the single pulse which is generated is more likely to terminate tachycardia. Nevertheless, it has been found that such a single-pulse technique is not maximally effective.

In the copending application of Spurrell et al, entitled "Rate-Related Tachycardia Control Pacer", Ser. No. 245,216, filed on Mar. 19, 1981, which application is hereby incorporated by reference, there is disclosed a tachycardia control pacer in which a burst of at least three pulses is generated following each tachycardia confirmation. The time intervals between pulses keep decreasing; the pulse rate thus continuously increases and the overall sequence is more accurately characterized as a "chirp" since its rate continuously increases. The successive time intervals between pulses decrease by the same fixed decrement. This type of increasing pulse rate during a single cycle of operation has been found to be effective in controlling tachycardia in some cases; the acceleration of pacing over a short interval results in stimulation at different phases of a tachycardia cycle and thus a greater likelihood of generating a pulse at the right time. Most important is the fact that the initial time interval, between the last heartbeat used to confirm tachycardia and the first pulse in the sequence, is related to the rate of the heartbeats and is equal to the heartbeat rate less the fixed decrement.

However, it has been found that neither of the aforesaid pulse sequences is effective in terminating all tachycardias. It is a general object of our invention to provide still another pulse stimulation sequence for terminating tachycardia, a sequence which is effective in many cases for which tachycardia cannot be terminated using prior art pulse sequences.

In accordance with the principles of our invention, a burst of pulses (typically, at least three to be effective, although the physician can program the number of pulses in each burst) is generated following each tachycardia confirmation. The pulses in each burst occur at a constant rate, the rate being independent of the tachycardia rate. If following the generation of a burst tachycardia is not terminated and tachycardia is still confirmed, then another pulse burst is generated, at a different rate. The same number of pulses is used in each burst, but the rates of the pulses in the bursts vary from cycle to cycle, each pulse-burst cycle occurring after a respective tachycardia confirmation. The scanning of the rate can be in either direction, although in the illustrative embodiment of our invention the scanning is in the direction of increasing rate. After a burst at the maximum rate is generated, the scanning resumes in the next cycle at the minimum rate.

The last burst rate which is successful in terminating tachycardia is registered in the pacer so that it is available for use following the next tachycardia confirmation. In this manner, the last successful rate is the first one to be used whan a new tachycardia episode is confirmed. It is only if the first burst at the last-successful rate is unsuccessful that rate scanning proceeds (starting with the last successful rate).

As in earlier tachycardia control pacers, the pacer of our invention can have several parameters programmed by the physician. In the case of our pacer, these include the number of pulses which are generated in each burst, as well as the minimum pulse rate. (Although it is possible to provide a pacer in which the incremental change in the rates of successive bursts can also be programmed, in the illustrative embodiment of our invention successive bursts during a scanning sequence have their inter-pulse intervals reduced by 6 milliseconds.) As in earlier tachycardia control pacers, the pacer of our invention can also be programmed to induce tachycardia so that the physician can observe whether the device successfully terminates the condition rapidly with a particular set of programmed parameter values.

Figure 3:
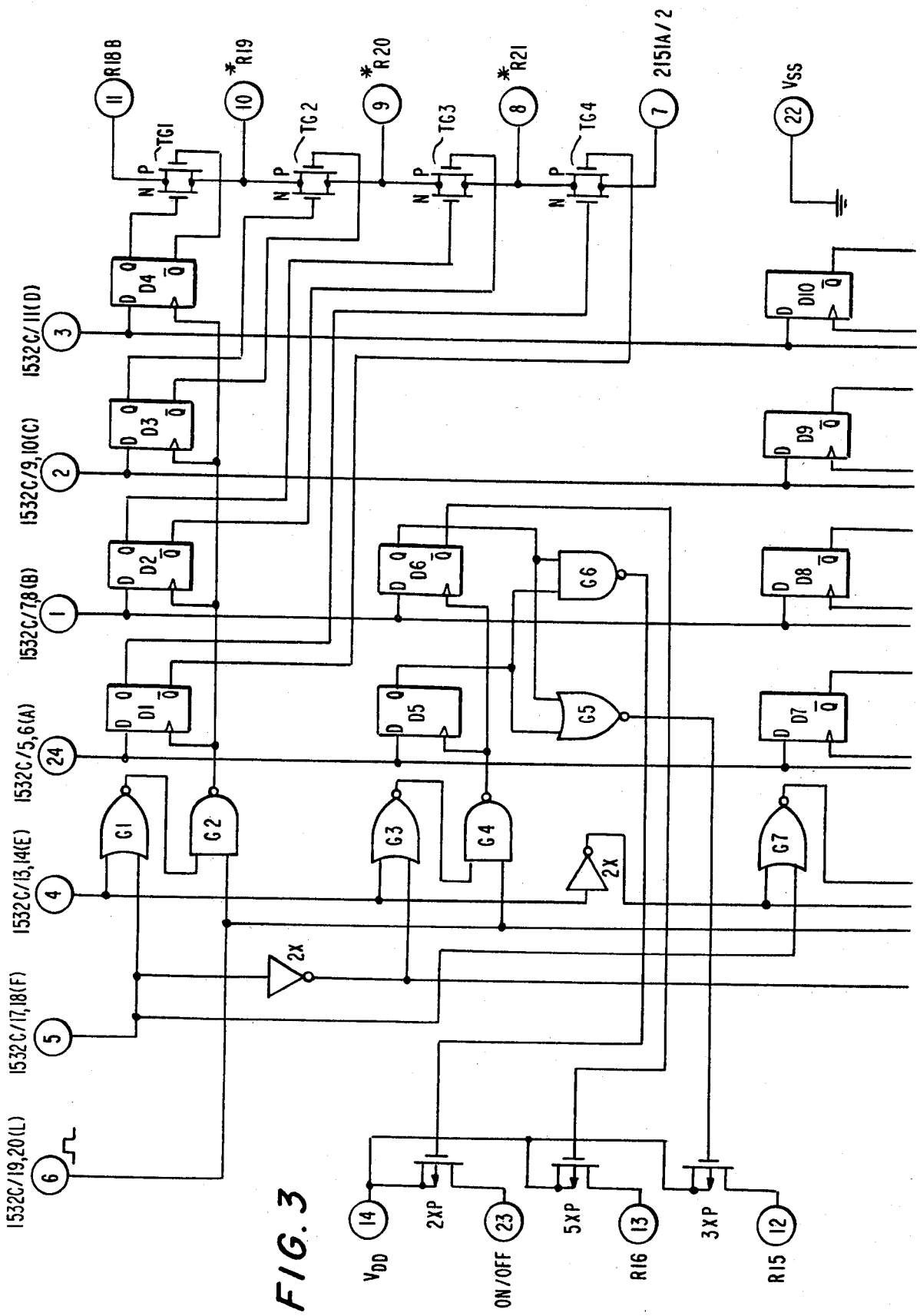
Figures 4, 4A:
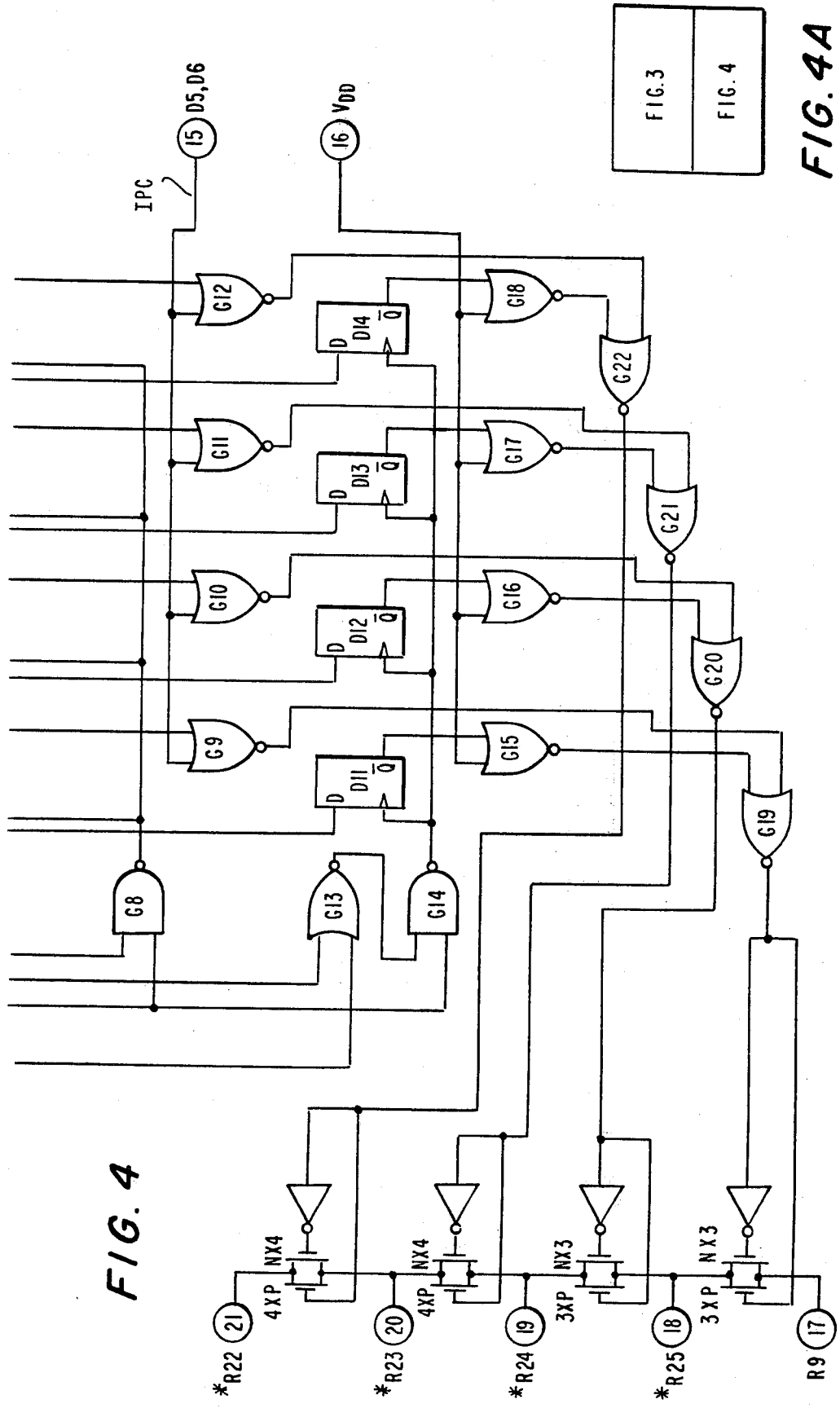
Figure 5:
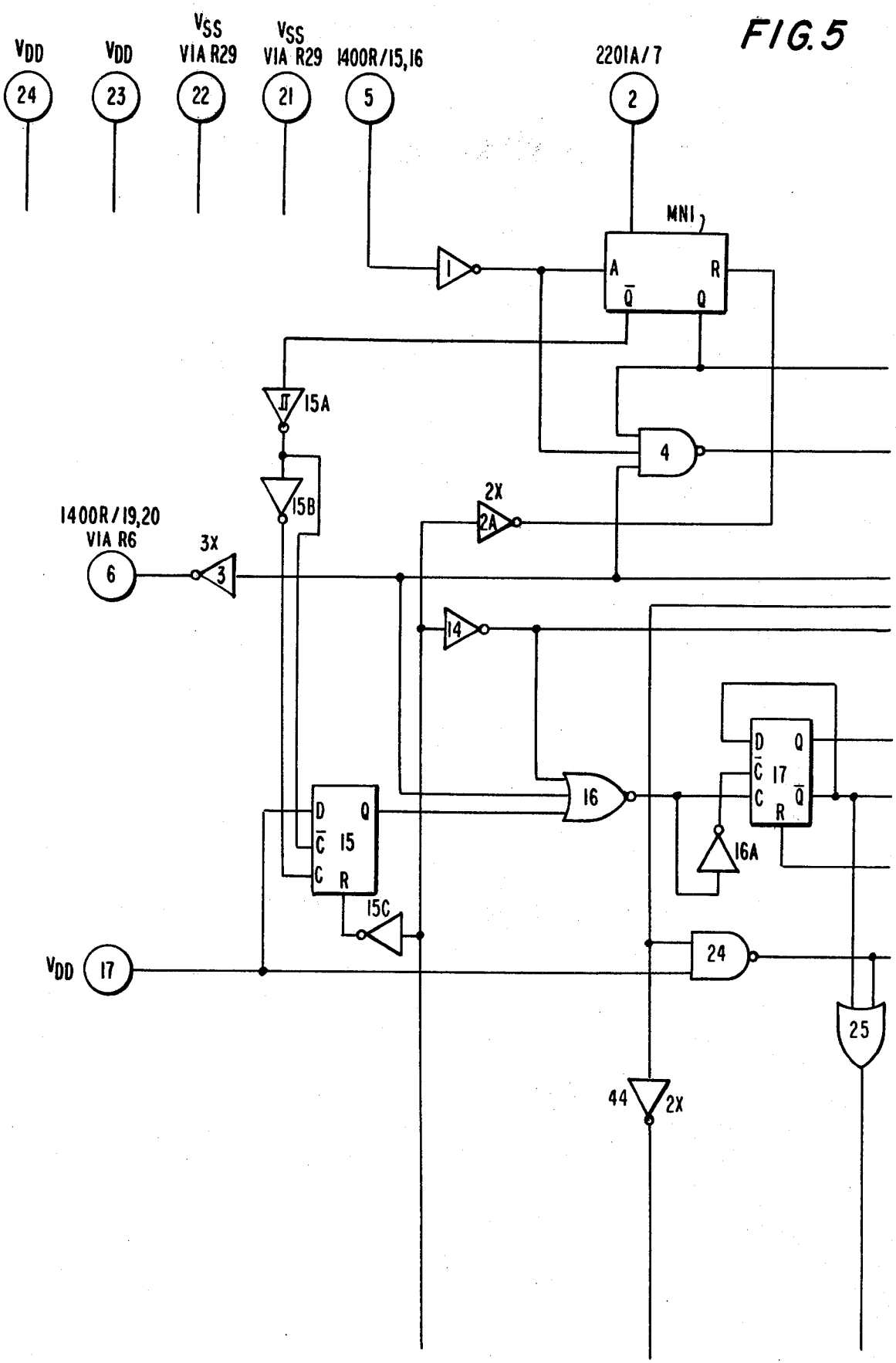
Figures 7, 8A:
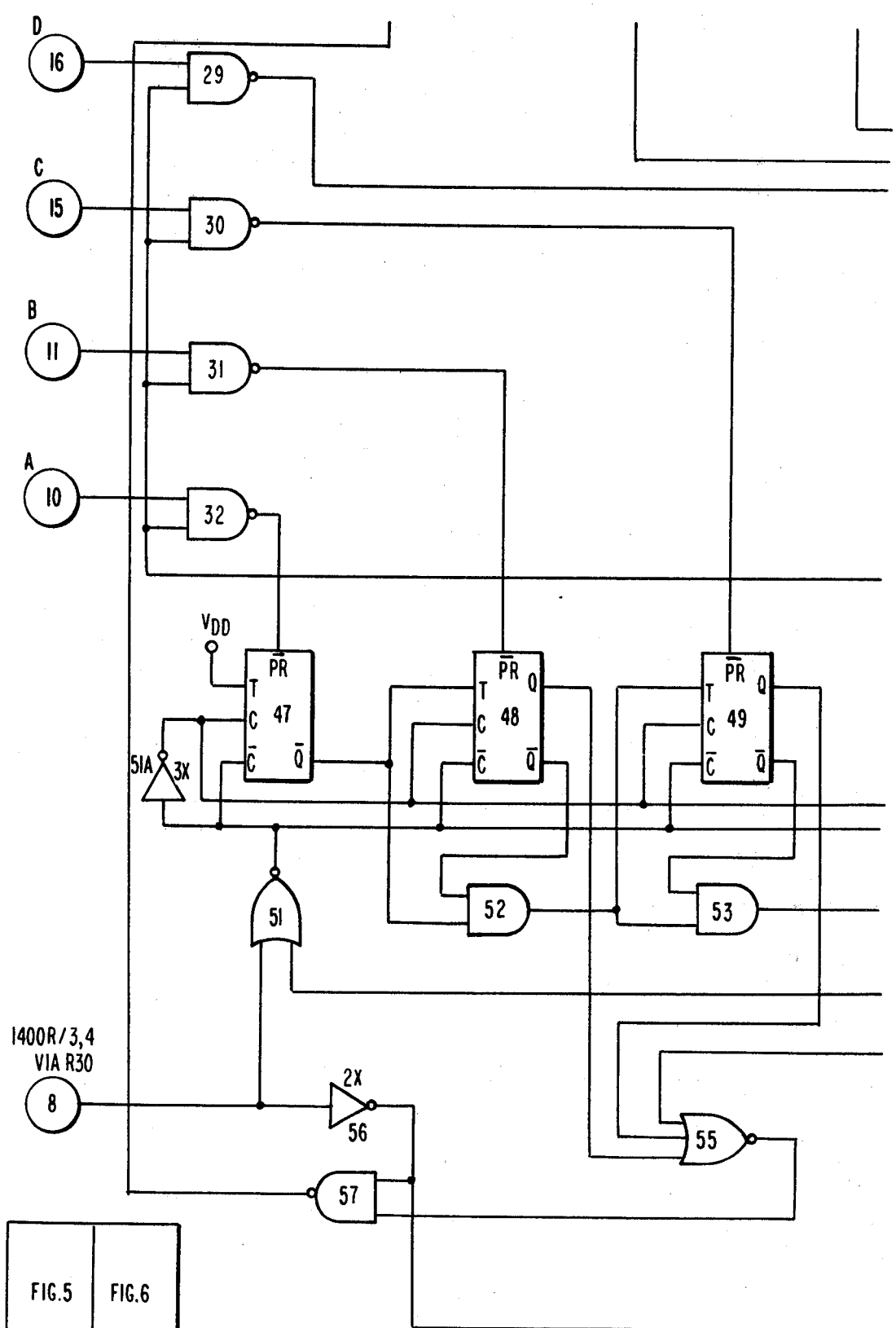
Figure 8:
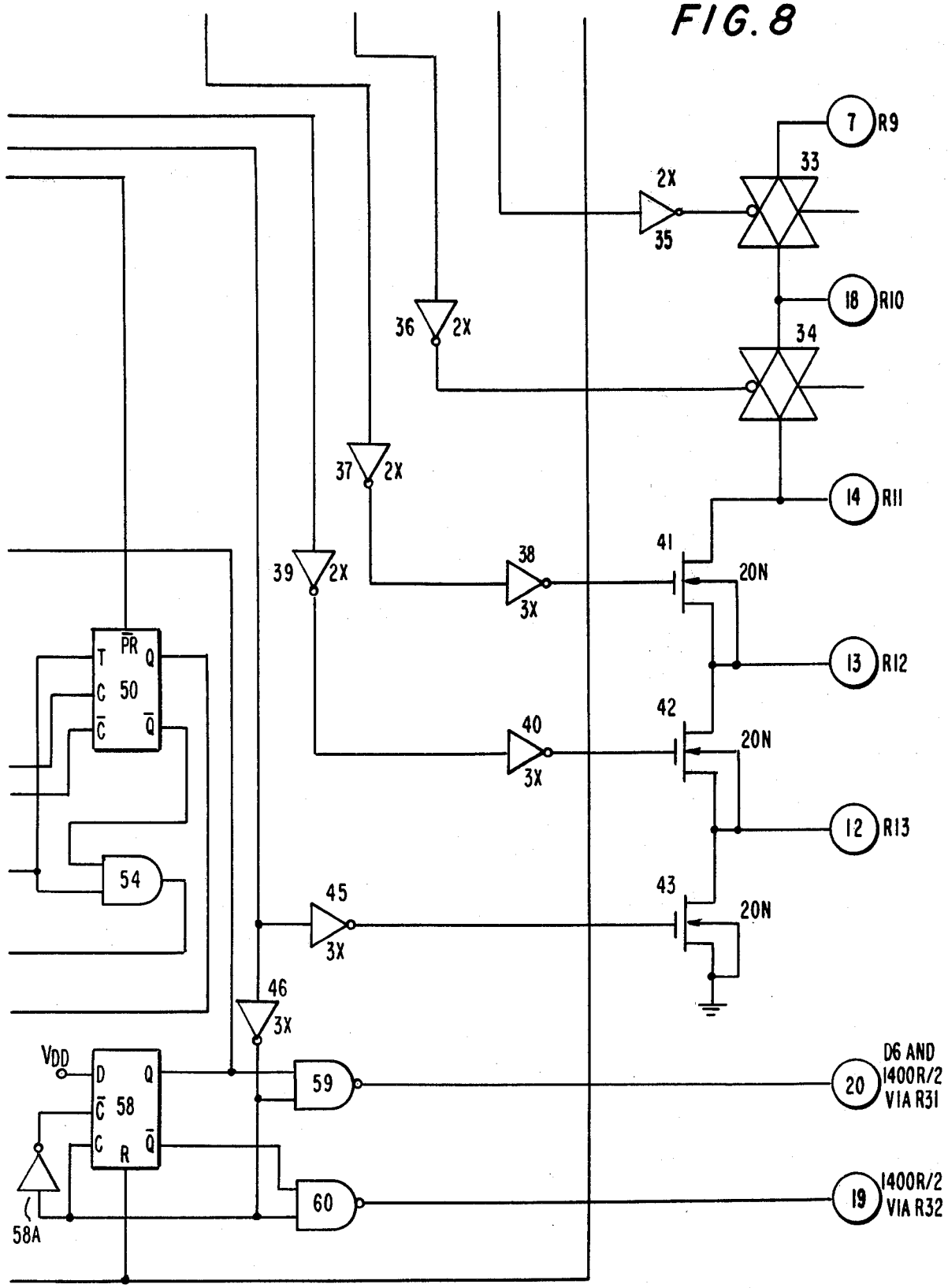
Figure 9:
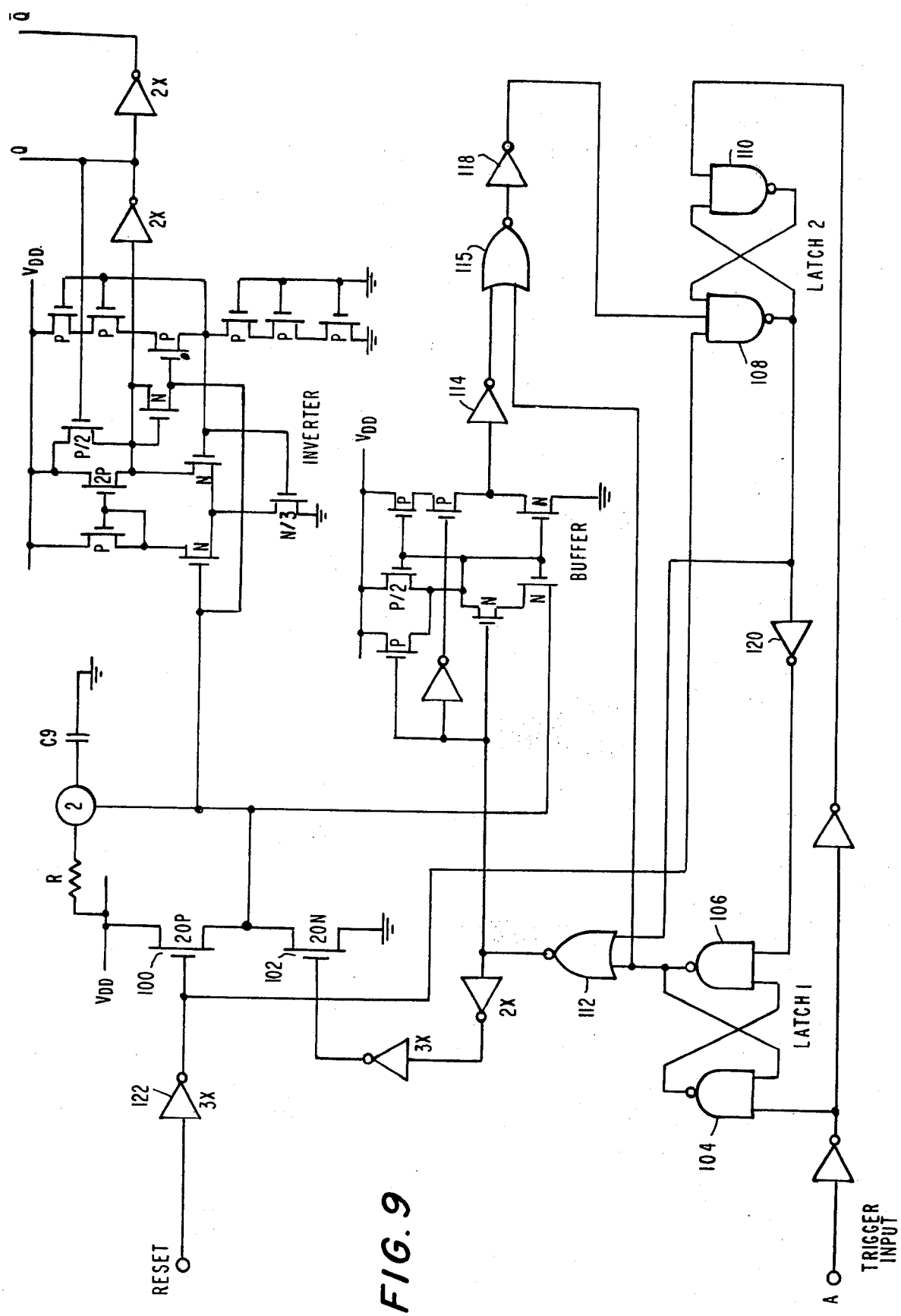

Further objects, features and advantages of our invention will become apparent upon consideration of the following detailed description in conjunction with the drawing, in which:

FIGS. 1 and 2, arranged as shown in FIG. 2A, depict the illustrative embodiment of our invention;

FIGS. 3 and 4, arranged as shown in FIG. 4A, depict the circuitry contained in chip IC4 of FIG. 2;

FIGS. 5-8, arranged as shown in FIG. 8A, depict the circuitry contained in chip IC3 of FIG. 2; and FIG. 9 depicts the details of monostable multivibrator MN1 which is shown only in block form on FIG. 5.

MONOSTABLE MULTIVIBRATOR: FIG. 9

Chip IC3 on FIG. 2 is the most complex of the five chips IC2–IC5 shown in FIGS. 1 and 2. The details of chip IC3 are depicted in FIGS. 5–8. One of the elements on the chip is multivibrator MN1 on FIG. 5. The operation of the multivibrator, from a system point of view, is very straight-forward. It is a re-triggerable device which generates a positive pulse at its Q output each time a trigger is received at the A input. If another trigger is received before the multivibrator has timed out, the Q output remains high for another timing period. The multivibrator is used to confirm tachycardia, and to understand the system operation the details of the multivibrator are unimportant. In order that the description of the system not be complicated by the details of the multivibrator operation, it would be best to consider the multivibrator at this point so that in the system description the detailed operation of the element can be ignored.

In FIG. 5, multivibrator MN1 is shown as having five inputs/outputs. The Q output is normally low in potential and $\overline{Q}$ output is normally high. A positive potential at the reset (R) input resets the multivibrator in this state. Upon receipt of a positive trigger pulse at the trigger (A) input, however, the Q output goes high and the $\overline{Q}$ output goes low. The duration of the pulse is controlled by various components connected to pin 2 on chip IC3. Referring to FIG. 2, it will be noted that pin 2 on chip IC3 is connected to capacitor C9, the other end of which is grounded through 200-ohm resistor R29. (The junction of the resistor and capacitor also serves as the $V_{SS}$ connection to chip IC3 at pins 21,22, as shown on FIG. 5.) Pin 2 on chip IC3 is also connected to a resistor chain, the first resistor of which is R21, as shown on FIG. 2. As will be described below, some of the resistors in the chain are shorted depending upon how the pacer has been programmed. But the total impedance determines the programmed "tachy rate", that is, the minimum inter-beat interval which, if exceeded, will abort a tachycardia confirmation cycle.

The multivibrator is shown in detail on FIG. 9. The reset and trigger inputs are shown on the left of the drawing, and the Q and $\overline{Q}$ inputs are shown in the upper right corner. Pin 2 of chip IC3 is shown connected on FIG. 9 to capacitor C9, just as the pin is shown connected on FIG. 2. However, instead of showing the complete resistor chain on FIG. 9, as it is shown in FIG. 2, the resistor chain is simply shown by a single impedance designated R.

On FIG. 9, $V_{DD}$ represents the battery potential, nominally 2.8 volts. Conventional symbols are employed to represent CMOS P-channel and N-channel enchancement-mode transistors, with designations such as P/2 or 2P referring to relative "on" impedances, that is, a 2P device conducts twice as much current as a P device for the same gate-source bias. The other devices shown comprise standard CMOS gates; symbols such as 3X adjacent an inverter refer to the fact that three standard inverters are connected in parallel.

In the absence of any trigger inputs, both of transistors 100 and 102 are off. Capacitor C9 charges through the resistor chain symbolized by the single resistor R from the positive supply, and pin 2 is at a high potential. The various devices which comprise the "inverter" function as a comparator. The 6 P-channel devices connected in series derive a threshold voltage which is equal to about half of the supply voltage. This threshold voltage is compared with the potential at pin 2. As long as the potential at pin 2 exceeds the threshold voltage, the Q output is low (thus the terminology "inverter", although the circuit also functions as a comparator). It is only when the capacitor voltage is less than the threshold voltage that the Q output is high and the $\overline{Q}$ output is low.

As will be described below, the trigger inputs represent heartbeats. The trigger input is normally low in potential. Gates 104,106 comprise a first latch, and gates 108,110 comprise a second latch. After the multivibrator times out, the output of latch 1 (output of gate 106) is high in potential and the output of latch 2 (output of gate 108) is low in potential. Latch 1 is considered to be reset, and latch 2 is considered to be set.

When a heartbeat is detected, the positive pulse at the trigger input causes latch 1 to set and the output of gate 106 goes low. Because both latch outputs are now low, and the two outputs are connected to the inputs of gate 112, its output now goes high. After being inverted twice, the high output of gate 112 causes transistor 102 to turn on. This has the effect of causing capacitor C9 to rapidly discharge through the device; the Q output now goes high and the $\overline{Q}$ output goes low.

The elements which comprise the "buffer" are a form of comparator, and they serve to detect when the capacitor voltage drops to about 100 millivolts. As long as the capacitor voltage exceeds 100 millivolts, the input to inverter 114 is low in potential. One input of gate 115 is thus high and the output of inverter 118 is similarly high; it is this high potential which holds latch 2 set with the output of gate 108 being low, as originally assumed. The second input of gate 115 is connected to the output of gate 106 which is also originally high. Thus in the absence of any heartbeats, both inputs to gate 115 are high, latch 2 remains set, and latch 1 remains reset. Even after a heartbeat is detected and the output of gate 106 goes low, latch 2 remains set because the output of inverter 114 is still high.

But as soon as capacitor C9 discharges through transistor 102 to the point at which its potential drops to 100 millivolts, the output of inverter 114 goes low. Since latch 1 is now set with the output of gate 106 also being low, the output of inverter 118 goes low. This causes latch 2 to reset, with the output of gate 108 going high. The high potential at the output of gate 108 causes the output of gate 112 to go low, and immediately causes transistor 102 to turn off. The high potential at the output of gate 108 is also inverted by inverter 120 to reset latch 1, with the output of gate 106 going high once again. The high potential at the output of gate 106 now sets latch 2 once again (or as soon as the trigger pulse terminates), since the output of gate 106 is connected to an input of gate 115. Consequently, latch 2 is set once again in its quiescent condition just as latch 1 is reset in its quiescent condition. Although the output of gate 108 no longer holds transistor 102 off, it is now the high output of gate 106 which holds the transistor off. The capacitor now starts to charge once again through the resistor chain.

It is thus apparent that following each heartbeat and the discharge of capacitor C9, the Q output of the multivibrator goes high and the $\bar{Q}$ output goes low. As soon as the capacitor charges to the threshold level of the inverter, in a time dependent upon the magnitude of impedance R, the output pulse terminates and the Q output goes low once again with the $\bar{Q}$ output going high. But if another heartbeat is detected before the capacitor can charge to the threshold level, the charging cycle begins all over again as soon as the capacitor discharges through transistor 102, and the Q output remains high. Thus the Q output remains high as successive heartbeats are detected, without going low between them, only if the heartbeats are detected at a rate fast enough to prevent capacitor C9 from charging to the threshold voltage of the "inverter". The multivibrator is re-triggerable in the sense that each trigger input extends the output (positive potential at the Q output) for another time-out interval. As will be described below, this is the basic mechanism for detecting a tachycardia episode—as long as four heartbeats are detected after an initial triggering of the multivibrator, without the Q output of the multivibrator going low, then it is assumed that a tachycardia episode has been detected. If any pair of successive heartbeats are separated by a time interval which exceeds that required for capacitor C9 to charge to the threshold level, then the Q output of the multivibrator goes low. As will be described below, this aborts the tachycardia confirmation counting cycle. By programming the value R, the physician can determine the heartbeat rate which if exceeded will result in tachycardia detection. The effective rates which the physician can program vary between 130 and 225 beats per minute. (As will be described below, the physician can also "fool" the pacer by programming it to a "tachy rate" of only 40 beats per minute; this results in the pacer treating normal beats as a tachycardia episode, the pacer automatically generates "premature" stimuli in an effort to terminate non-existing tachycardia and this may actually induce a real tachycardia. By then reprogramming the pacer with a normal "tachy rate", the physician can check whether the programmed time parameters, are effective in terminating tachycardia.)

The reset input on FIG. 9 is normally low in potential. The high output of inverter 122 holds transistor 100 off and also holds one input of gate 108 high so that latch 2 can operate as described above. But when the reset input is high, as will be described below, the output of inverter 122 is low in potential and transistor 100 turns on. This has the effect of rapidly charging capacitor C9 through transistor 100 from the $V_{DD}$ supply, and the Q output of the multivibrator remains low (as though heartbeats were not being detected at all) for as long as the reset input is high. The low input now applied by inverter 122 to one input of gate 108 causes the output of latch 2 to be forced high, and this in turn holds the output of gate 106 high even if trigger pulses are received. In this way, transistor 102 remains off independent of trigger inputs.

The reason for the relatively "complex" multivibrator is that the battery supply, while nominally 2.8 volts, can drop as low as 2.2 volts with age. In order that the time-out remain constant independent to the battery potential, the circuit is designed to provide a threshold which is equal to about half of the battery supply, no matter what its value. This is the function of the six P-channel tansistors in the "inverter" circuit. Since the battery potential determines both the rate at which capacitor C9 charges and the threshold potential, the time-out is independent of the precise potential level.

It should be noted that this type of multivibrator is standard in the art. In fact, Motorola Inc. markets a component (MC14538) which is just such a multivibrator; its time-out period is independent of supply voltage. But the circuit of FIG. 9 is preferred because it operates on low voltages and draws very little current (thereby extending device life).

Overview of the System and General Chip Descriptions

The overall system is shown in FIGS. 1 and 2, and it includes five chips IC1-IC5. Chips IC1, IC2 and IC5 are standard-type chips used in heart pacers; they will be described below only in terms of their input and output signals, and the functions which they perform. Chips IC3 and IC4 are specially-designed chips and they will be described in detail. The circuitry included on chip IC4 is shown in FIGS. 3 and 4, and the circuitry included on chip IC3 is shown in FIGS. 5-8.

Each of the five chips on FIGS. 1 and 2 is designated not only by one of the labels IC1-IC5, but also by its chip number, e.g., chip IC5 bears number 1532C. On each of the two sets of chip drawings of FIGS. 3 and 4, and FIGS. 5-8, each pin of the respective chip is labelled not only by number, but also by its connection in the overall system. For example, pin 5 of chip IC3 (see FIG. 5) has adjacent to it the designation 1400R/15,16. This means that pin 5 of chip IC3 is connected to pins 15 and 16 of chip IC2 (1400R). Referring to FIGS. 1 and 2, it will be seen that pin 5 of chip IC3 is indeed connected to pins 15 and 16 of chip IC2. As another example, pin 21 of chip IC4 (see FIG. 4) bears the designation R22. This means that pin 21 of the chip is connected to resistor R22, as shown in FIGS. 1 and 2.

In FIGS. 1 and 2, it will be noted that several of the resistors have an asterisk preceding their labels; this symbol identifies a resistor as being a high-stability component. Several of the resistors are not provided with component values, and instead are labelled "SOT". Such a designation refers to the fact that the value of the respective component is "selected on test", i.e., a component value is selected which provides proper operation. The component ranges for the resistors designated as SOT are as follows:

R13: 8.06–11.5 M
R8: 220–420 K
R17: 4.81–8.66 M
R18B: 8.2–11.5 M
R27: 1.2–2.4 M
R15: 3.9–6.8 K

It will also be noted that many of the inputs and outputs of the chips on FIGS. 1 and 2 have two pin designations. For example, chip IC2 on FIG. 1 is connected to the positive supply rail via two pins 23, 24. It is standard practice in the pacer art to provide such double connections for increased reliability; even if one pin connection fails, because the two pins are internally connected on the chip, the chip still functions for its intended purpose as long as the other pin connection remains intact.

Chip IC1 is a conventional sense amplifier/comparator, and chip IC2 is a conventional timing oscillator/pulse doubler; both chips are standard chips used in the manufacture of heart pacers and are available from Amalgamated Wireless Microelectronics Pty. Ltd. of Sydney, Australia. Chip IC5, used by Telectronics Pty. Ltd. in its standard line of heart pacers, is a standard-type "program controller" chip; this chip detects reed closures, as controlled by an external programmer, and sets programmable parameters accordingly in the pacer. Techniques for programming pacers are standard in the industry, the design of program controls is well known in the art, and there is nothing unique about use of the particular chip No. 1532C insofar as the present invention is concerned; any conventional programming technique may be employed, as long as it provides the signals to be described below. Chip IC4 serves primarily to store programmed values and to control the shorting out of selected resistors in two resistor chains. Chip IC3 contains most of the logic which is unique to the present invention.

Programming of the Pacer; Chips IC4 and IC5, And the Resistor Chains

Before proceeding to a detailed description of the system operation, the manner in which the pacer can be programmed will first be described. In this way, it will be understood how the various latches contain parameter values when the data stored in these latches are described below as controlling respective functions. The programming is essentially independent of the system operation, and it will be convenient to describe it first so that the pacing functions can be considered below without having to digress for the purpose of describing the programming.

Chip IC5 on FIG. 1 (1532C) is a conventional-type program controller. The $V_{DD}$ connection to the chip is at pins 23,24. (As shown at the bottom of FIG. 1, the positive supply potential, V+, is derived from a 2.8-volt cell, with a filter capacitor C12 connected across it.) Reed switch RS1 is connected to pins 15,16, with resistor R26 serving as the pull-up for the switch. Under the influence of an external magnetic field, the normally-open reed switch is closed, and a ground potential is applied to pins 15,16. Resistor R27 and capacitor C11 are the timing components for an internal oscillator on the chip. Incoming reed pulses must be properly timed if an incoming programming sequence is to be treated as valid; the internal oscillator on the chip determines whether valid programming pulses are received. For example, if the reed switch is held closed for a long time period by placing an external magnet over the chest of a patient, because the resulting pulse at pins 15,16 is too long relative to the oscillator timing, the reed closure has no effect on the outputs of chip IC5.

There are five parameters which may be programmed. The first is pulse width, i.e., the width of each pulse generated by the pacer. Two bits are used to represent the pulse width, and there are thus four possible values. The first value is 0—effectively disabling the pacer since no pulses are generated. The three pulse widths which can be controlled when the pacer is operative are 0.25, 0.35 and 0.6 milliseconds.

The second parameter is sensitivity. A single bit is used to control sensitivity of the sense amplifier/comparator chip IC1, as is standard in the pacer art. The two sensitivities are 1 millivolt and 2 millivolts.

The third parameter is the maximum inter-pulse interval, i.e., the minimum pulse rate. Scanning of the pulse rate begins with this value the first time that the pacer is called upon to terminate tachycardia after the initial programming. (Thereafter, the successful pulse rate is retained, and subsequent scanning begins with the retained value.) There are 12 maximum inter-pulse interval values from which the physician can choose, and thus four bits are required to represent them. The values are 200, 210, 230, 250, 270, 290, 300, 320, 340, 360, 380 and 390 milliseconds.

The fourth parameter which can be programmed is the number of pulses in each burst which is to be generated, up to a maximum of fifteen. As a practical matter, a burst should contain at least three pulses, despite the fact that burst lengths of one and two pulses may be programmed.

The fifth parameter which can be programmed is "tachy rate"; this is the parameter which determines the width of the pulse generated by monostable multivibrator MN1 (FIG. 9) each time that a heartbeat is detected. Four bits are used to represent the tachy rate, and the eight possible values are 40, 130, 140, 150, 165, 180, 200 and 225 beats per minute. For example, if a tachy rate of 150 beats per minute is selected, the pulse width of the multivibrator is adjusted such that the Q output of the multivibrator will remain high if, after any beat, four successive beats are detected at a rate which exceeds 150 beats per minute, with the inter-beat interval between any two successive beats not exceeding 60/150 or 400 milliseconds.

The program controller chip IC5 responds to incoming reed switch pulses in four programming steps. Although the four steps will be described in a particular sequence, the first three can be interchanged; it is only the fourth step which must always be the fourth step in a programming sequence.

There are seven output conductors from chip IC5, labeled A–F and L. These outputs are connected to seven inputs of chip IC4, the inputs bearing similar letter designations. The seven inputs to chip IC4 appear at the top of FIG. 3, FIGS. 3 and 4 showing the details of chip IC4. The A–D inputs are data bits which represent parameter values. The E and F inputs are address bits which select particular latches for the storage of the data bits. Input L is a latch control input. The program controller chip IC5 decodes incoming reed switch pulses, and applies two address and four data bit values to its outputs A–F. The chip then applies a positive pulse to the L output which actually controls latching of the data bits in a set of latches determined by the address bits. (The program controller chip IC5 also sets an impedance value at its output pin 12, but this occurs during the fourth programming step, and will be described below.)

The first programming step involves setting the tachy rate. The four bit values which represent the rate and appear on conductors A–D are applied to the D inputs of register flip-flops D1–D4 on FIG. 3. The E and F address bits are both low during this step, and consequently the output of gate G1 is high to enable one input of gate G2. When the latch pulse is applied to the other input of gate G2 over conductor L, the gate output goes low. This output is coupled to the clock input of each of the four flip-flops. At the end of the latch pulse, the rising edge at the clock input of each flip-flop clocks the four tachy-rate data bits into the four flip-flops.

The second programming step involves storing the four bits which represent the maximum inter-pulse interval in the latch which comprises register flip-flops D7–D10 on FIG. 3. The four data bits on lines A–D are connected to the D inputs of the flip-flops just as they are connected to the D inputs of flip-flops D1–D4. It is now gates G7 and G8 which control latching of the data in the flip-flops. The output of gate G8 is connected to the clock input of each of the flip-flops, and the latch input pin 6 is connected directly to one input of gate G8, just as it is connected to one input of gage G2. Just as the other input of gate G2 is connected to the output of gate G1, the other input of gate G8 is connected to the output of gate G7. One of the inputs of gate G7 is connected directly to the F address input, and the other input of gate G7 is connected through an inverter to the E address input. Thus an EF address of 10 causes the output of gate G7 to go high, and at the trailing edge of the latch pulse the minimum-rate data bits are clocked into flip-flops D7–D10.

During the third programming step, the E and F address bits represent a 01 combination. It will be noted that the E address bit input on FIG. 3 is connected directly to one input of gate G3, and the F address bit input is connected through an inverter to the other input of gate G3. The output of gate G3 is connected to one input of gate G4, the other input to which is connected to latch input pin 6. Consequently, gate G4 clocks flip-flops D5 and D6 at the end of the latch pulse. The A and B data bits are connected to the D inputs of these two flip-flops, and these two data bits represent the four pulse width values (off, and 0.25, 0.35 and 0.6 milliseconds). The two pulse-width bits are stored in the two flip-flops during the third programming step.

In the last programming step, the four data bits which represent the number of pulses in each burst appear on lines A–D, together with an address 11 on the E and F lines. Gates G13, G14 control the latching of the data bits in flip-flops D11–D14 just as gates G1, G2, G3, G4 and G7, G8 control latching of the data bits in the three other sets of latches during the first three programming steps. It will be noted, however, that both inputs to gate G13 are now derived from inverters which are connected to the E and F address inputs. Consequently, in the fourth programming step the E and F outputs of chip IC5 are both high.

The data stored in flip-flops D11–D14 are not actually used; because pin 16 is held high on FIG. 4, the outputs of gates G15–G18 are always low and are not affected by the flip-flops. The flip-flops are not required in the present invention; they are shown in the drawing only because the actual chip utilized includes them, and they are necessary for other applications of the chip. Their inclusion in the overall system of the present invention is in effect negated by tying pin 16 to a high potential. The A–D data bits transmitted in the last programming step remain latched at the outputs of chip IC5. They are extended to pins 10, 11, 15 and 16 of chip IC3 (see FIGS. 1 and 2), and this is how they are available to control the number of pulses in each burst.

During the fourth (always the last) programming step, the sensitivity of the sense amplifier/comparator chip IC1 may be determined by a single bit which controls an external resistor connection to pin 12 of chips IC5. Pin 12 is coupled to the input filter circuit for chip IC1, and it directly controls the sensitivity of chip IC1 as is standard in the pacer art. The reason that the fourth programming step must always be the last one is that a separate latch is not provided for the sensitivity control (or for the number of pulses in each burst). Chip IC5 itself serves as the sensitivity latch, just as it serves as the latch for the data bits which control the number of pulses in each burst.

In the description of monostable multivibrator MN1 (FIG. 9) above, it was explained that pin 2 of chip IC3 (see FIGS. 2 and 5) is connected to the junction of capacitor C9 and a resistor chain. The resistor chain is shown generally by the symbol R on FIG. 9, but actually comprises resistors R17, R18B, R18A, R19, R20 and R21 (see FIG. 2). The tachy-rate flip-flops D1–D4 on FIG. 3 have their Q and $\bar{Q}$ outputs connected to respective inputs of transmission gates TG1–TG4. Each gate, when turned on, shorts a pair of pins to each other, the five pins 7–11 being connected to the various resistors in the resistor chain just described. Thus if all of the transmission gates are off, all of the resistors are in the chain. On the other hand, when any two adjacent output pins are shorted to each other through a respective transmission gate, the resistor or resistors connected between the two pins are shorted and do not contribute to the total impedance. It is in this manner that the four tachy-rate flip-flops determine the minimum rate which must be exceeded for tachycardia confirmation, the physician being able to select from among eight different rates (one of which is "artificial" in that it is not really a legitimate tachy rate, but rather is programmed in order to attempt to induce tachycardia).

Chip IC2 on FIG. 1 generates the stimulating pulses, as will be described below. The width of each pulse is controlled by the potential which appears at input pins 11,12. Pins 11,12 are connected to the junction of resistors R14, R15 and R16. While resistor R14 is connected to the positive supply rail, the other two resistors are connected to output pins 12 and 13 of chip IC4. These two output pins, together with output pin 23 and pulse-width flip-flops D5 and D6 (FIG. 3), determine the pulse width.

Each of pins 12,13 and 23 is either floating or held at the potential of the positive supply ($V_{DD}$ at pin 14, FIG. 3). If both of flip-flops D5 and D6 have bits of value 1 stored in them, their Q outputs are both high. Since both Q outputs are connected to inputs of gate G6, the output of gate G6 is low and the connected P-channel transistor between pins 14 and 23 is held on. Consequently, the positive potential at pin 14 is extended to on/off pin 23. Referring to FIGS. 1 and 2, it will be noted that pin 23 of chip IC4 is connected through resistor R7 to pin 2 of chip IC2. Whenever the potential at pin 2 is high, no pulses are generated by chip IC2. Consequently, when a data bit combination of 11 is stored in flip-flops D5 and D6, the device is inhibited from operating. For each of the other three combinations of data bits, the output of gate G6 is high and pin 23 floats. Pacer pulses can be generated, and the pulse width depends on the potentials which appear at pins 12 and 13.

When each of flip-flops D5,D6 contains a 0, the two inputs of gate G5 are low, and its output is high; the P-channel transistor connected between pins 12 and 14 is off so pin 12 floats. Since the $\bar{Q}$ output of flip-flop D6 is high in such a case, the P-channel transistor between pins 13 and 14 is also off, and pin 13 floats. Referring to FIG. 2, resistors R15,R16 are effectively out of the circuit, and the only connection to pins 11,12 of chip IC2 is that of resistor R14 whose other end is connected to the positive supply rail.

With a 1 in flip-flop D5 and a 0 in flip-flop D6, pin 13 still floats. But the output of gate G5 is now low so that pin 12 is connected to the positive supply at pin 14. Referring to FIG. 2, resistor R15 is now effectively in parallel with resistor R14 between pins 11,12 of chip IC2 and the positive supply.

The last case is that in which flip-flop D5 contains a 0 and flip-flop D6 contains a 1. The output of gate G5 is once again low due to one of its inputs being connected to the Q output of flip-flop D6. The Q output of the same flip-flop is low. Consequently, both of pins 12,13 are connected to pin 14 through their respective coupling transistors. Effectively, all of resistors R14, R15 and R16 are connected in parallel between pins 11,12 of chip IC2 and the positive supply, to provide the third possible pulse width.

Referring to FIG. 2, output pins 12, 13, 14, 18 and 7 of chip IC3 will be described below as selectively controlling the shorting out of resistors in a series chain comprising resistors R9–R13. One end of the resistor chain is connected to ground (either through resistor R13, or directly through pin 12 of chip IC3 when the chip grounds the pin). The resistor chain then continues from the junction of pin 7 and resistor R9 to resistor R25. In a similar manner, resistors R22–R25 are connected in series in the overall chain, with selected ones of the four resistors being shorted out depending upon whether pin pairs such as 18,19 are internally shorted in chip IC4. AThe resistor chain terminates in resistor R8 which is connected to capacitor C8. The resistor chain and the capacitor control the timing of chip IC2, that is, when a stimulating pulse is generated. The resistor chain is used to control the time interval between stimulii in each pulse burst. It is chip IC3 which shorts out selected resistors from among those in the group R9–R13 to control scanning of the pulse rate, i.e., a different pulse rate after each tachycardia confirmation until tachycardia is terminated; as different pairs of pins among pins 12, 13, 14, 18 and 7 are shorted to each other during the scanning of the pulse rate, the time interval between successive pulses decreases in 6-millisecond discrete steps. But the maximum inter-pulse interval (when none of resistors R9–R13 are shorted) is controlled by chip IC4 and the selective shorting of resistors R22–R25. The circuitry on FIG. 4 (part of chip IC4) shorts pairs of adjacent pins among pins 17–21 in order to control the maximum inter-pulse interval. The control is exercised by flip-flops D7–D10, to the exclusion of unused flip-flops D11–D14.

Output pins 19 and 20 of chip IC3 (FIG. 2) are connected through respective diodes D5 and D6 to the IPC conductor at input pin 15 of chip IC4. Input pin 16 of chip IC4 is held high permanently. Referring to FIG. 4, when timing is not required and both of input pins 15 and 16 are high in potential, the outputs of all of gates G9–G12 and G15–G18 are low. Thus the inputs of all of gates G19–G22 are low, and all of the gate outputs are high. The high potentials hold off the four respective transmission gates which are connected between respective pairs of pins in the group comprising pins 17–21.

When an inter-pulse interval must be timed, conductor IPC goes low. As will be described below, while the return of the IPC conductor through resistor R33 to the battery potential normally holds pin 15 high, whenever pulse timing is required one of pins 19 or 20 of chip IC3 is low. Thus the IPC inputs to gates G9–G12 have no effect on the circuit operation, and the gate outputs depend upon only the data stored in flip-flops D7–D10, since the Q outputs of these flip-flops are connected to respective inputs of the gates. Since the outputs of gates G15–G18 always remain low because pin 16 is held high in potential, these gates do not affect the operations of gates G19–G22. The latter gates are controlled only by the outputs of gates G9–G12, that is, the data bits stored in flip-flops D7–D10. It is in this manner that this group of flip-flops controls the shorting of resistors R22–R25 to set the maximum inter-pulse interval. During successive burst cycles, it is resistors R9–R13 which are selectively shorted out so that the inter-pulse interval decreases in 6-millisecond decrements from burst to burst. The combination of resistors R22–R25 which is involved in the timing is always the same, the combination being controlled by the data latched in flip-flops D7–D10.

Brief Description of Chips IC1 And IC2

Before proceeding to a detailed description of the overall system, it will be helpful to review the operations of chips IC1 and IC2. Both of these chips (1438B and 1400R) are commercially available devices and they perform standard functions. For this reason, it will suffice to describe the input and output signals of the two chips, without describing how they work internally.

The two electrode connections (IND and STIM) as shown on the left side of FIG. 1. The indifferent electrode is grounded. The stimulating electrode is coupled both to pins 20,21 of chip IC1 and to pins, 9,10 of chip IC2. Chip IC1 is a standard sense amplifier/comparator which serves to detect a heartbeat. As described above, the sensitivity is determined by program controller chip IC5 (pin 12). The components connected to chip IC1 are all standard, and the sense amplifier/comparator operation is the same as that to be found in prior art pacers. Whenever a heartbeat is detected, a positive pulse appears at output pins 9,10.

Chip IC2 is a timing oscillator. It is the "heart" of a conventional pacer, but is used in the illustrative embodiment of the invention only as a timer and pulse generator. A positive pulse appearing at pins 21,22 is internally coupled through the chip to pins 19,20. The pulse is coupled through capacitor C6 to pins 17,18. A trigger input at pins 17,18 resets the internal oscillator in chip IC2 and starts a new timing cycle. Chip IC2 can operate in either the synchronous or the inhibit mode. In the former, a stimulating pulse is generated at pins 9,10 whenever a heartbeat is detected in order to reinforce it; and in the latter, such a reinforcement pulse is not generated. Because pin 1 is grounded, chip IC2 operates in the inhibit mode.

If a positive potential is applied through resistor R6 to capacitor C6, the trigger pulses are not extended from pins 19,20 through the capacitor. Thus when pin 6 of chip IC3 (FIG. 2) is high, it inhibits the detection of heartbeats. A low potential applied to pins 17,18 also prevents the trigger inputs from resetting the timer. When reed switch RS1 is operated, the low potential applied through "hot carrier" diode D2 to pins 17,18 causes the oscillator in chip IC2 to run free and pacing pulses to be generated continuously. (The term "hot carrier" refers to the fact that the voltage drop across the diode is 0.3 volts, not the usual 0.6 volts.) The pulses are in fact not generated continuously, but the reason will be described below.

Pacing pulses are generated at pins 9,10 of chip IC2, and are coupled through capacitor C5 to the stimulating electrode. Coincident with each pacing pulse, a negative pulse is generated at pins 3,4.

A negative pulse is also generated at pins 15,16 whenever a pacing pulse is delivered to the stimulating electrode, just as a negative pulse appears at pins 3,4. However, a negative pulse also appears at pins 15,16 whenever a heartbeat is detected, in which case a negative pulse does not appear at pins 3,4 since chip IC2 is operated in the inhibit mode. Capacitor C4 is the charge storage capacitor which discharges through pins 9,10 whenever a stimulating pulse is required. Capacitor C8, connected between pin pairs 15,16 and 13,14 is the rate timing capacitor. This capacitor, as well as resistor R8 and all of the resistors previously described in the resistor chain, determine the rate at which the internal oscillator of chip IC2 operates.

The potential at pins 11,12 of chip IC2 controls the width of each pulse which is generated, as described above.

Lastly, a high potential applied to pin 2 of chip IC2 disables the chip from generating pacing pulses at all. When pin 23 of chip IC4 (FIG. 2) is high in potential, as described above, the potential extended over the on/off conductor and through resistor R7 prevents pacing pulses from being generated. Capacitor C7 is normally charged through resistors R26, R4 so that it also normally inhibits pulse generation. Chip IC2 is thus held off most of the time. When a pulse burst is required, capacitor C7 is discharged through diode D3 and resistor R31, and held discharged by diode D4 and resistor R32, as will be described below.

With these remarks in mind, the system operation will now be described. The system logic is controlled by chip IC3. In the following description reference should be made of FIGS. 5-8 (chip IC3), as well as to FIGS. 1 and 2 which depict the connections from chip IC3 to the remainder of the system. It should be noted that two pin connections to chip IC3 are not shown. One of these pin connections is merely a test point and is not involved in the system operation; the other pin, pin 9, is not used at all and both are omitted from the drawing for the sake of clarity. (Pin 3 of chip IC3 is in fact connected to the Q output of multivibrator MN1, shown in block form on FIG. 5 and in detail on FIG. 9.)

System Operation

When a heartbeat is detected, a negative pulse appears at pins 15,16 of chip IC2, as described above. This pulse is extended to pin 5 of chip IC3, as shown in FIGS. 1 and 2. The negative pulse is inverted by inverter 1 (FIG. 5) and a positive pulse is applied to the trigger (A) input of the monostable multivibrator. A positive pulse now appears at the Q ouput of the multivibrator, its duration being dependent upon the "tachy rate" programmed by the physician (see description above of chip IC4 and resistors R17-R21). The Q output is connected to one input of gate 4. The same pulse which triggers the multivibrator is applied to a second input of gate 4. The third gate input is normally high in potential. Thus as long as the output of inverter 7B is high, the output of gate 4 is pulsed low whenever a heartbeat is detected.

Flip-flops 5, 6 and 7 comprise a standard ripple counter which is initially reset to 000. With the $\bar{Q}$ output of each of flip-flops 5 and 7 initially high, and since they are connected to inputs of gate 7A, the gate output is low. The output is inverted by inverter 7B to apply a high potential to the third input of gate 4.

Flip-flop 5 is toggled on the trailing edge of each output pulse from gate 4. If the counter is not reset, as successive heartbeats are detected and the counter cycles from 000 to 100, the $\bar{Q}$ output of at least one of flip-flops 5 and 7 remains high, and the output of gate 7A remains low. But when the fifth pulse is counted without the counter having been reset during the sequence, the $\bar{Q}$ output of gate 7A goes high. The output of inverter 7B now goes low to disable gate 4; no further pulses are counted.

The Q output of multivibrator MN1 is connected to an input of gate 10. Whenever the multivibrator times out, that is, the Q output goes low without the output pulse being extended by the arrival of another trigger input before the time-out is over, one input to gate 10 goes low. The output of gate 7A is connected to the other input of gate 10, and this input is thus low in potential until five heartbeats have been counted. Thus each time-out of the multivibrator, as long as the counter has not reached a count of five, causes the output of gate 10 to go high.

One input of gate 9 is connected to the output of inverter 14, whose input is connected to the output of gate 57. As will be described below, the output of gate 57 is normally high, and thus one input to gate 9 is normally low. Consequently, whenever the Q output of the multivibrator goes low at the end of a time-out and the output of gate 10 goes high, the output of gate 9 goes low, and the output of inverter 9A goes high. Since the gate output is connected to the reset input of each flip-flop in the counter, this causes the three-stage counter to reset to 000.

Thus whenever a heartbeat occurs after a preceding heartbeat with an inter-beat interval longer than the reciprocal of the "tachy rate", the counter is reset and the tachycardia confirmation cycle starts all over again. But if five rapid heartbeats are detected in succession, the Q output of the multivibrator does not go low to reset the counter. Even though it may go low after the fifth beat is counted, the output of gate 7A is now high and it is connected to an input of gate 10; thus the output of inverter 9A is locked low as soon as a count of five is reached so that the counter cannot be reset even if the multivibrator times out.

The tachycardia confirmation test involves four rapid beats, not five, even though five beats are counted. The first beat merely serves as a time reference for the second. The basic test is whether four rapid beats occur in succession, each of which is too soon after the respective previous beat. Once tachycardia is confirmed, the counter remains at a count of five and further counting is inhibited. The low potential which is now at the output of inverter 7B holds gate 4 off.

This same potential is inverted by inverter 3 and thus a positive potential appears at pin 6 of chip IC3 (FIG. 5). As indicated on the left of FIG. 5, and as shown in FIGS. 1 and 2, the positive potential is extended through resistor R6 to pins 19,20 of chip IC2. Any further heartbeats which are detected by chip IC1 are thus ignored. Also, since the count of five was reached in the first place by a negative pulse appearing at pin 5 of chip IC3, which pulse resulted from chip IC2 having detected a heartbeat and generated a negative pulse at pins 15,16, the oscillator on chip IC2 starts timing a new cycle. As will become apparent, this timing determines the first inter-pulse interval (which is really the interval between the last detected heartbeat and the first stimulus). The reason for inhibiting heartbeat detection in chip IC2, by holding pulse 19,20 high as just described, is that the oscillator on chip IC2 is used to determine when the stimuli should be applied, and this timing function should not be interfered with by any heartbeats which may occur.

When the output of gate 7A first goes high, several things happen in addition to those described above. Gate 24 is enabled since the second of its inputs is now high, its other input being held high permanently by the battery potential at pin 17. The positive potential at the output of gate 7A is inverted by inverter 44, and inverted once again by inverter 46 to clock flip-flop 58. Since the D input of the flip-flop is connected to the positive supply, the flip-flop is set and its Q output goes high to enable gate 59. The positive potentials which now appear at the outputs of inverters 46 and 45 are applied to the second input of gate 59 and also to the gate of transistor 43. The transistor turns on, and the output of gate 59 goes low.

As shown on FIG. 2, the output of gate 59 is extended from pin 20 of chip IC3 through diode D6 to pin 15 of chip IC4. It will be recalled that when the IPC conductor goes low, chip IC4 (FIGS. 4 and 5) shorts out preselected ones of resistors R22–R25 for controlling the programmed (longest) inter-pulse interval. It will also be recalled that capacitor C7 on FIG. 1 is initially charged to a positive potential, the positive potential at pin 2 of chip IC2 preventing the generation of stimulating pulses. Now that a first stimulus is required, however, a low potential must be applied to pin 2 of chip IC2. Because pin 20 of chip IC3 is now low in potential, capacitor C7 discharges through diode D3 and resistor R31 so that a stimulus can be generated.

Referring to FIGS. 1 and 2, the overall resistor chain involved in the timing of chip IC2 consists of resistors R9–R13, R22–R25 and R8, different ones of the resistors being shorted out at different times. With transistor 43 on FIG. 8 now on, pin 12 of chip IC3 is grounded. As shown on FIG. 2, this shorts out resistor R13 from the resistor chain. The actual inter-pulse interval which is now timed depends upon two sets of resistors, R9–R12 and R22–R25. The latter set is pre-selected and the same resistors are always placed in the chain whenever a timing function is required. If all of the resistors R9–R12 are included in the chain, then the preselected combination of resistors R22–R25 provides the longest inter-pulse interval, as programmed by the physician. But the actual interpulse interval (pulse rate) in any cycle is determined by which of resistors R9–R12 happen to be shorted, i.e., how many 6-millisecond decrements have already taken place during previous burst cycles. Depending upon the total impedance of the resistor chain, the oscillator on chip IC2 times out and results in the generation of a first stimulating pulse. Coincident with this pulse, and as described above, a negative pulse is generated at pins 3,4 on chip IC2. This pulse is coupled through resistor R30 on FIG. 1 to pin 8 of chip IC3. As shown on FIG. 7, the negative pulse at pin 8 is inverted by inverter 56 and thus resets flip-flop 58. Gate 59 now turns off, and it is gate 60 whose output now goes low.

Chip IC2 can generate additional pulses only if pin 2 is not held high to disable pulse generation. It is pin 20 of chip IC3 going low which discharges capacitor C7 rapidly to permit the first pulse to be generated. Although pin 20 goes high after the first stimulus is generated, pin 19 of chip IC3 (FIG. 8) is now low. The low potential is extended through resistor R32 and diode D4 to hold capacitor C7 discharged so that additional pulses can be generated. Chip IC2 continues to generate pulses for as long as pin 19 of chip IC3 remains low. Successive negative pulses at pin 8 (FIG. 7), coincident with the generated stimulii, have no effect on flip-flop 58 which remains reset. (The manner in which the number of pulses in each burst is controlled will be described below.) The low potential at pin 19 of chip IC3 is also extended through diode D5 to the IPC conductor at pin 15 of chip IC4. In this manner, chip IC4 controls the continued shorting of the same resistors in resistor chain R22–R25.

Figure 6:
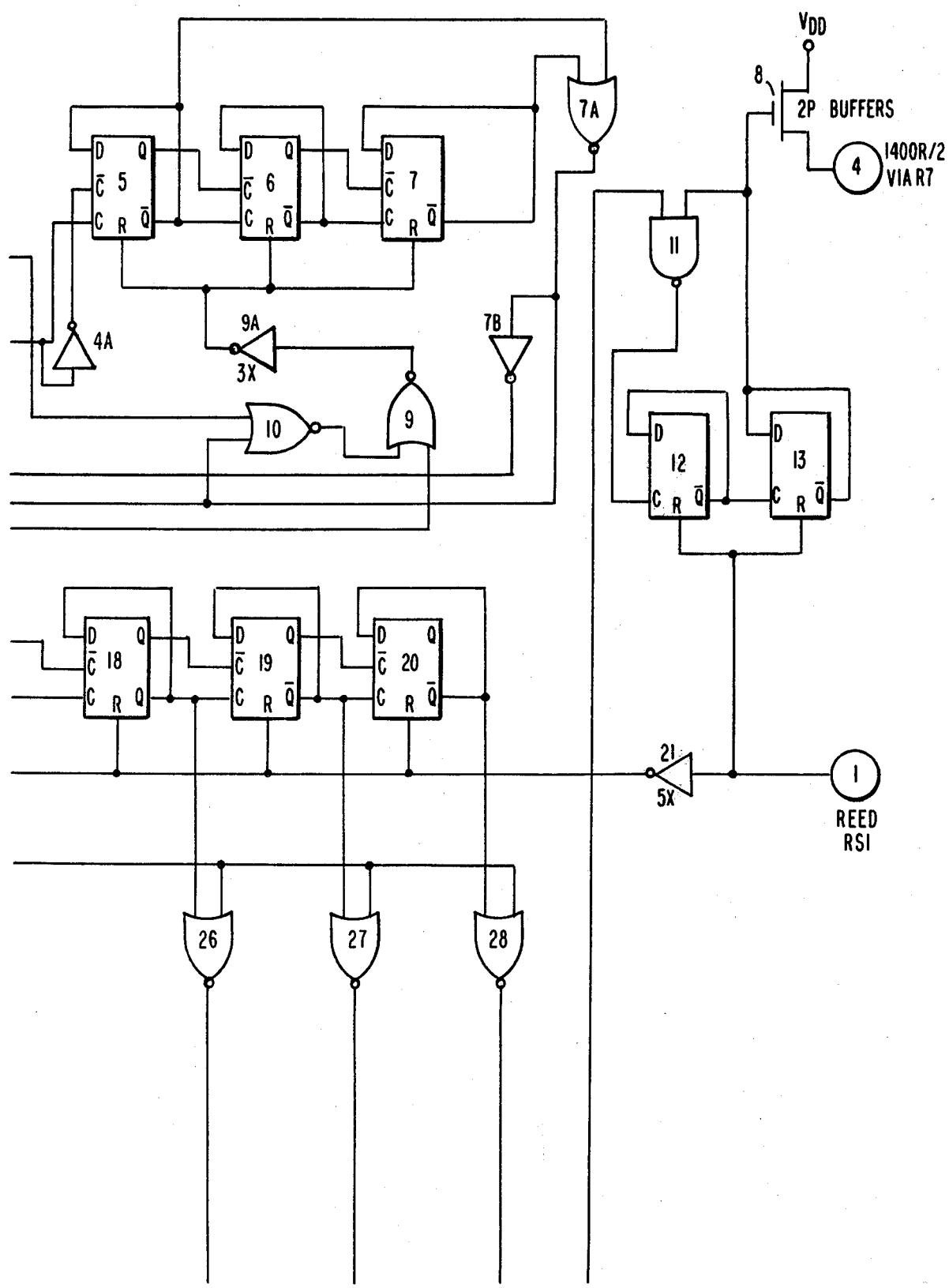

Reed switch RS1 on FIG. 1 is connected to pin 1 of chip IC3. Referring to FIG. 6, it will be noted that each time the reed switch is operated and a ground potential appears at pin 1, inverter 21 applies a positive reset pulse to all of flip-flops 17–20. As will be described below, these are the flip-flops which control the decrementing of the inter-pulse interval by 6-millisecond decrements between pulse bursts. During programming, each time the reed switch is operated all of the flip-flops are reset. This has the effect of inserting all of resistors R9–R12 (FIG. 2) in the resistor chain so that the longest (programmed) inter-pulse interval is first timed. Whenever a cycle does not result in tachycardia termination, flip-flops 17–20, which are arranged as a four-bit counter register, have their count incremented so that in the next cycle the inter-pulse interval is decremented by 6 milliseconds. After the fifteenth decrement, the interval is set to its highest value once again, as the counter cycles from 1111 to 0000.

It is gate 16 which controls the incrementing of the counter which comprises flip-flops 17–20. The count representing the number of 6-millisecond decrements of the inter-pulse interval is incremented whenever the output of gate 16 goes high. It is important that gate 16 not operate immediately after a pulse burst has concluded. That is because if tachycardia has been terminated, the count in flip-flops 17–20 should be retained so that the same pulse rate will be used when the next tachycardia episode is confirmed; downward scanning of the inter-pulse interval (upward scanning of the burst rate) always begins with the last successful value. (It is only when a tachycardia episode is encountered following initial programming that the scanning begins with the minimum burst rate, since all of the flip-flops 17–20 are reset.)

Flip-flop 15 is clocked by the rising edge of the pulse at the Q output of the multivibrator. The rising edge is not necessarily sharp, and for this reason an inverter 15A with hysteresis is utilized to form clock pulses. Because the D input of the flip-flop is held at a high potential, a positive step in the Q output of the multivibrator causes the flip-flop to be set.

The flip-flop is reset when the output of gate 57 goes low, and the output of inverter 15C goes high, at the end of every pulse burst as will be described below. When the flip-flop resets, its Q output goes low, this output serving as one input to gate 16. The output of inverter 7B is connected to a second input of gate 16. This output is low while a pulse burst is being generated, but when gate 57 controls the resetting of flip-flop 15 it also controls resetting of the counter comprising flip-flops 5–7. As soon as the latter flip-flops reset, the output of gate 7B goes high. Thus, the output of gate 16 remains low even though the output of flip-flop 15 no longer holds it low.

Gate 16 should not operate to increment the counter which comprises flip-flops 17–20 because when the tachycardia confirmation circuit is first enabled to operate once again, there is no way of knowing whether tachycardia has yet been terminated. If it has been terminated, the output of gate 16 should remain low so that flip-flop 17 is not toggled. In the event the output of flip-flop 15 goes low before the output of inverter 7B goes high, two inputs to gate 16 would be low, and the output would go high to toggle flip-flop 17. In order to prevent this, the output of gate 57 is coupled through inverter 14 to a third input of gate 16. While the output of gate 57 is low the output of inverter 14 is high, so that the output of gate 16 remains low. By the time the output of gate 57 goes high once again, the output of inverter 7B has gone high so that it can hold the output of gate 16 low.

Thus by the time that the output of gate 57 reverts to its normally high state (it is pulsed low only momentarily after each pulse burst), the tachycardia confirmation circuit is enabled to operate once again, and flip-flop 15 is reset with its Q output being low. If tachycardia has not been terminated, multivibrator MN1 does not time out as it is continuously re-triggered by heart-beats which are once again detected (since pin 6 on FIG. 5 is now low), and the Q output remains low after the first multivibrator triggering. Consequently, following the next tachycardia confirmation, when the output of inverter 7B goes low, all three inputs to gate 16 are low in potential and the output goes high to clock flip-flop 17. Since tachycardia has not been terminated, the inter-pulse intervals which are now timed are decremented by 6 milliseconds.

On the other hand, if tachycardia has been terminated, the multivibrator times out and its Q output goes high. Flip-flop 15 is now set and its Q output goes high. Thus the output of gate 16 is held low. Even though another tachycardia episode may be confirmed some time later, when the output of inverter 7B goes low it does not result in the toggling of flip-flop 17. This allows the previously successful burst rate to be the first one which is used.

It will be recalled that immediately upon tachycardia confirmation, the output of gate 7A goes high to enable one input of gate 24 (FIG. 5). The other input to this gate is always high. Thus the output of gate 24 is low, and it enables the operation of each of gates 25-28. The outputs of these four gates are controlled by respective flip-flops 17-20, and the output of each of gates 25-28 is coupled through one or two inverters to an input of a respective one of transmission gates 33, 34, 41 and 42. As seen on FIG. 2, these are the four gates which control the selective shorting of resistors R9-R12 at pins 7, 18, 14 and 13 of chip IC3. (Gates 33 and 34 each include a P-channel and an N-channel transistor connected in parallel; because these gates control resistors in the middle of the resistor chain, a full drive may not be available to fully turn on a single N-channel device. By providing two opposite-type transistors in parallel, they compensate for each other, as is known in the art. Single-transistor gates 41 and 42 are sufficient to short out resistors R11 and R12 since these resistors are at the end of the chain, closer to ground potential.)

When flip-flops 17-20 represent a count of 0000, all of resistors R9-R12 are in the resistor chain. The resistors are weighted in the approximate ratio 1:2:4:8 so that as flip-flops 17-20 count in binary fashion, successive decrements of the initial delay are all the same.

Referring to FIG. 2, it will be recalled that resistor R13 is shorted out by transistor 43 (FIG. 8) immediately upon tachycardia confirmation. Resistor R13 is nominally 10 M. In the absence of tachycardia, this artificially high resistor is placed in the resistor chain in order to make the time-out period of the oscillator in chip IC2 so high that no pacing pulses can be generated; even though pin 2 of chip IC2 is held high in the absence of tachycardia to prevent the generation of pacing pulses, chip IC2 also requires a resistive connection to pins 13,14. But when stimuli must be generated, resistor R13 is removed from the circuit so that the only resistors which control inter-pulse interval timing are resistors R9-R12, R22-R25 and R8. The reason for providing resistor R8 is that if the maximum possible pulse rate has been programmed, all of resistors R22-R25 are shorted out, and if all of resistors R9-R12 are similarly shorted out at the end of the scan of the burst rate, then there would be no resistance connected to pins 13,14 of chip IC2. Resistor R8 serves as the minimum resistance for controlling a minimum inter-pulse interval when the counter which comprises flip-flops 17-20 counts all the way to 1111 and shorts out all of resistors R9-R12.

Thus far the system operation has been described only insofar as chip IC2 generates pulses continuously, following tachycardia confirmation, at a rate dependent upon the minimum rate represented in flip-flops D7-D10 (FIG. 3) and the incremental value represented in flip-flops 17-20, the rates of successive bursts increasing (and cycling back to the minimum rate) until tachycardia is terminated. At the end of each burst, the output of gate 57 (FIG. 7) was described as going low momentarily in order to reset flip-flop 15 (FIG. 5). There remains to be described how the number of pulses in each burst is determined by the four data bits at outputs A-D of chip IC5 (FIG. 1), how gate 57 is pulsed, and the other functions which it controls.

Flip-flop 58 (FIG. 8) is set as soon as tachycardia is confirmed. When its Q output goes high, one input of each of gates 29-32 goes high. The other inputs to these gates, the A-D bits latched in chip IC5 which represent the number of pulses required in each burst, are inverted and extended through the gates to the preset inputs of flip-flops 47-50. The flip-flops are interconnected in a standard configuration which causes the flip-flops to function as a synchronous down counter. The count contained in the counter is decremented from the initial value (the number of pulses required in a burst) each time that the output of gate 51 goes low.

The output of gate 52 is high only when each of flip-flops 47 and 48 represents a 0 (with its $\overline{Q}$ output high). The output of gate 53 is high only when the output of gate 52 is high and flip-flop 49 represents a 0. Similarly, the output of gate 54 is high only when the output of gate 53 is high and flip-flop 50 represents a 0. Thus until the total count is decremented down to 0, the output of gate 54 is low, and gate 51 functions simply to invert the potential at pin 8.

As described above, pin 8 is pulsed low whenever chip IC2 generates a pulse. (It is pin 8 going low when the first pulse is generated which results in the resetting of flip-flop 58 on FIG. 8 as described above.) At the trailing edge of each pulse, when the output of gate 51 goes low, all of flip-flops 47-50 are clocked and the count of the pulses remaining to be generated is decremented. Each flip-flop switches state, when it is clocked, only if its T (toggle) input is high; only flip-flop 47 switches state whenever it is clocked because its T input is held high.

When the count decrements from 0100 to 1000 (with the least significant bit being to the left and being represented by flip-flop 47), for the first time each of flip-flops 48-50 represents a 0. The output of gate 55 goes high to enable gate 57. The next negative pulse at pin 8, corresponding to the last pulse to be generated in the burst, causes the output of gate 57 to go low for as long as the pulse persists. At the trailing edge of the pulse, the count decrements to 0000 and the output of gate 54 finally goes high. The output of gate 51 is now held low so that a count of 0000 remains in the counter. The maximum number of pulses in a burst which can be programmed by the physician is 15 since this is the maximum count which can be present in the counter, but the physician can select some other number; whichever number is selected, that number of pulses will be present in each burst.

If the physician programs data bits A-D each to represent a 0, a "burst" of one pulse is still generated (just as it is if the data bits represent 1000). Although the output of gate 54 is high and gate 51 cannot decrement the count in flip-flops 47-50, the output of gate 57 is not pulsed low to stop pulse generation until a negative pulse appears at pin 8 on FIG. 7, that is, until one pulse has been generated.

While it is true that flip-flop 58 controls the pre-setting of flip-flops 47-50 when it is set in the 1 state, and the first pulse which arrives at pin 8 does so while the flip-flop is still in this state (since it is this pulse which resets the flip-flop), the count represented by flip-flops 47-50 is nevertheless decremented by this first pulse. That is because it is the leading edge of the pulse which resets flip-flop 58 to disable pre-setting gates 29-32, and it is the trailing edge which decrements the count—after the PR inputs of flip-flops 47-50 are no longer energized.

As described above, when the output of gate 57 is pulsed low flip-flop 15 is reset. This primes gate 16 to decrement the count in flip-flops 17-20 if the tachycardia confirmation circuit next determines that tachycardia has not been terminated. The negative pulse at the output of gate 57 is inverted by inverter 2A in order to reset monostable multivibrator MN1. The negative pulse at the output of gate 57 is also inverted by inverter 14 to reset flip-flops 5-7, through gate 9 and inverter 9A; in this manner the tachycardia confirmation circuit can determine whether tachycardia has been terminated, in which case flip-flop 15 is set so that eventually, if another episode is detected, the count in flip-flops 17-20 will not have changed. On the other hand, if tachycardia has not been terminated, flip-flop 15 is still reset when the output of gate 7B goes low after four fast heartbeats have been detected; the count in flip-flops 17-20 is incremented and another burst, at a faster rate, is generated in an attempt to cause the patient's heart to revert to sinus rhythm.

It should be noted that as soon as flip-flops 5-7 are reset after the burst, the output of inverter 7B goes high and pin 6 on FIG. 5 goes low. This allows chip IC2 to detect heartbeats once again so that trigger pulses are once again applied to multivibrator MN1 via pin 5 on FIG. 5. It is only during the generation of a pulse burst that chip IC2 is prevented from detecting heartbeats so that it can function in a free-running mode.

Most conventional heart pacers are designed so that a physician can determine the battery potential in order that the remaining life of the pacer may be ascertained. Often this is accomplished by placing a magnet over the patient's chest in the vicinity of the pacer, whereupon the closing of a reed switch causes the pacer to generate pulses at a continuous rate which is dependent upon the battery potential. But continuous pulses are not generated by a tachycardia control pacer. Thus there is no apparent way for the physician to determine the battery potential.

It would also be advantageous were there some way for the physician to ascertain the programmed (maximum) value of the inter-pulse interval. This is especially true in the case of a patient who consults a physician other than the one who programmed the device, in which case there may be no record of the programmed value. While the physician could monitor the ECG waveform of the patient and measure the maximum (programmed) value, there is a problem with this approach. Even assuming that tachycardia can be induced so that stimuli are generated, a complete scanning cycle may take several minutes (allowing for tachycardia confirmation following each pulse burst). Since the scanning does not necessarily begin with the maximum inter-pulse interval, the physician may actually have to observe an ECG waveform for several minutes before the maximum interval can be ascertained. It would be highly desirable to provide a mechanism by which the programmed value could be determined rapidly.

There is one other capability which would also be advantageous and that is to provide a simple mechanism whereby the patient can completely inhibit operation of the pacer. The physician can accomplish this by programming the device so that pin 23 of chip IC4 (on/off) is high in potential, as described above. But if the patient is feeling discomfort, it is also advisable to provide him with a simple mechanism for disabling the pacer operation until the physician can program it off.

Flip-flops 12,13, transistor 8, and the several gate connections to pin 1 on FIG. 6 allow all of the aforesaid desirable features to be added to the pacer at little additional cost and with a minimum of complexity.

The reset inputs of flip-flops 12,13 on FIG. 6 are connected to pin 1. Thus during normal operation when reed switch RS1 (FIG. 1) is open, a positive potential is applied to the reset inputs of the flip-flops and they are held reset. But if a magnet is applied to close the reed switch, pin 1 is grounded through the switch so that the reset input to the flip-flops is lifted. The closing of the reed switch also serves two other functions. The first is to allow capacitor C7 to discharge through resistor R4 (FIG. 1). The capacitor is normally charged through resistors R4 and R26 to prevent any pacing pulses from being delivered, the capacitor first being discharged through diode D3 and resistor R31 when pin 20 of chip IC3 (FIGS. 2 and 8) goes low following tachycardia confirmation, and then being held discharged by the low potential on pin 19 of chip IC3 through diode D4 and resistor R32. In the same way, capacitor C7 discharges through resistor R4 and the reed switch to allow chip IC2 to generate pulses. Although resistor R4 is large in magnitude and capacitor C7 does not discharge quickly when the reed switch is closed, that is of no moment; as will be described, the desired operation is the generation of a pair of pulses and what is important is the time between the two pulses, not when the first one occurs. (It should be observed that if the on/off conductor is high in potential, capacitor C7 remains charged through resistor R7 which is of much lower magnitude than resistor R4, and chip IC2 cannot generate any pulses even if the reed switch is closed. If the pacer has been programmed off, it remains off even if the reed switch is closed by a magnet.)

The other function performed by the reed switch is the pulling low of pins 17,18 of chip IC2 through diode D2 (FIG. 1). When these pins go low, chip IC2 operates in a free-running mode.

Assuming that a pulse burst is not in progress when the magnet is applied (if the magnet is applied during a pulse burst, then the resulting battery potential "reading" will not be valid), eventually capacitor C7 discharges through resistor R4 and chip IC2 starts to deliver pacing pulses at pins 9,10. With the delivery of each pulse, pins 3,4 go low as described above. In the usual way, a negative pulse is applied to pin 8 of chip IC3 (FIG. 7). Each negative pulse is inverted by inverter 56 and thus a positive pulse is applied to one input of gate 11 on FIG. 6. With flip-flops 12,13 being initially reset (as a result of pin 1 having previously been held high when the reed switch was open), the $\bar{Q}$ output of flip-flop 13 is high and thus the second input of gate 11 is enabled. When the output of gate 11 is pulsed low with the delivery of the first pulse from chip IC2, flip-flop 12 is set on the trailing edge. Flip-flops 12,13 comprise a standard two-bit ripple counter. The next pacing pulse results in the clocking of flip-flop 12 once again, since the $\bar{Q}$ output of flip-flop 13 is still high to enable gate 11 when the pulse arrives. But at the trailing edge of the pulse, when flip-flop 12 is reset and flip-flop 13 is set, the $\bar{Q}$ output of the latter flip-flop goes low to disable gate 11. At the same time, gate 8 turns on and applies the positive battery potential to pin 4. Referring to FIGS. 1 and 2, it will be seen that this positive potential charges capacitor C7 through resistor R7, just as does pin 23 of chip IC4 when the pacer is programmed off. Consequently, chip IC2 delivers only two pulses at pins 9,10.

The time interval between the two pulses is controlled in the usual manner by the resistor chain connected to pins 13,14 of chip IC2. None of the resistors in the overall chain is shorted out. It will be recalled that pin 12 of chip IC3 (FIG. 2) shorts out resistor R13 when a pulse burst is generated. The resistor is shorted out when pin 12 on FIG. 8 goes low under control of transistor 43, the transistor being turned on when the output of gate 45 goes high upon tachycardia confirmation. But there is no tachycardia confirmation now, so gate 43 remains off and resistor R13 is not shorted out. The low potential at pin 1 of chip IC3 (see FIGS. 1,2 and 6) due to the closing of the reed switch applies a positive potential through inverter 21 on FIG. 6 to the reset input of each of flip-flops 17–20. With all four flip-flops reset, the inputs to all of gates 25–28 are high, and all of the gate outputs are low to hold off transmission gates 33, 34, 41 and 42. Consequently, all of resistors R9–R12 are similarly placed in the resistor chain.

The outputs of gates 59 and 60 on FIG. 8 are high since there has been no tachycardia confirmation; thus the IPC input at pin 15 of chip IC4 is high. Referring to FIG. 4, the inputs of all of gates G19–G22 are low, all of the gate outputs are high, and thus none of pins 17–21 are shorted to each other. Consequently, all of resistors R22–R25 remain in the resistor chain.

The net result is that the time interval between the two pulses generated by chip IC2 is the maximum, and is determined primarily by resistor R13. This maximum is selected so that the battery potential of 2.8 volts controls an inter-pulse interval of 1.5 seconds. As the battery potential decreases with age, the interpulse interval is increased proportionally since it takes longer for capacitor C8 (FIG. 1) to charge. All the physician has to do is to observe the patient's ECG waveform and to time the interval between the two pulses in order to ascertain the battery potential. This is similar to the prior art technique of using a magnet to control the rate of a conventional heart pacer in order to determine the battery potential, inasmuch as the time interval between the two pulses which are generated is equivalent to a "rate". Of course, in order to achieve the effect with a tachycardia control pacer, it is necessary to artificially control the generation of at least two pulses in the manner described, even though chip IC2 does not function as an ordinary pacer.

It should be noted that a relatively high value of resistance is used for resistor R13 in order that the interpulse interval will vary between approximately 1.5 and 1.7 seconds as the battery ages. Two pulses which occur this far apart (the separation should be at least one second) can have no deleterious effect on the beating of the patient's heart.

The physician can use a magnet in the manner described in order to determine the battery potential. But the patient can also use such a magnet to shut off the pacer so that it does not generate pulses even following tachycardia confirmation. Since pin 2 of chip IC2 is held at a high potential after two pulses are generated, for as long as the magnet is applied, the patient can hold the pacer off by holding the magnet in place. He may then go to see his physician (while still holding the magnet in place to keep the pacer off), and the physician can program the pacer permanently off by forcing pin 23 of chip IC4 high as described above. (Along the same lines, the patient might be furnished with a programmer of his own which would only be capable of programming the pacer off. Only the physician's programmer could control programming of the pacer on once again. A patient-operated pacemaker programmer of this type, although used for a completely different purpose, is disclosed in Loughman et al patent application Ser. No. 123,916 entitled "Patient-Operated Pacemaker Programmer", filed on Feb. 22, 1980, which application is hereby incorporated by reference.)

Upon removal of the magnet, flip-flops 12,13 on FIG. 6 are both reset once again when pin 1 goes high, transistor 8 turns off, and chip IC2 is no longer inhibited from generating stimulating pulses. The device resumes operating in the usual way.

As described above, programming of the device results in the resetting of flip-flops 17–20; each reed closure resets the flip-flops through inverter 21. Thus scanning always begins with the programmed value of interpulse interval since the decrement-controlling flip-flops are all reset. By monitoring the patient's ECG waveform and noting the first burst rate following tachycardia confirmation, the physician can immediately determine the programmed value without having to wait for this value to be reached perhaps several minutes later during the scanning. Of course, the physician can determine the rate parameter quickly only if there is some way to induce tachycardia so that stimuli are generated in the first place. It is also advantageous to allow the physician to induce tachycardia so that he can observe whether the pacer is functioning at all, and also so that he can experiment with different programmed parameters to see which are the most effective in terminating tachycardia.

A mechanism is therefore provided to induce tachycardia which does not require any additional components. It will be recalled that the tachy rates which can be programmed by the physician are all within the range 130–225 beats per minute, except for the lowest tachy rate of 40 beats per minute. The tachy rate of 40 beats per minute is not a "real" rate because even normal sinus rhythm results in tachycardia confirmation—normal heartbeats occur at a rate greater than 40 beats per minute. But by allowing such a low rate to be programmed, the physician may possibly induce tachycardia.

What happens is that a normal sinus rhythm results in tachycardia confirmation and the generation of a pulse burst. Preferably, at the same time that the tachy rate is programmed to 40 beats per minute, the pacer should also be programmed to generate the maximum number of pulses in a burst, fifteen. The stimuli soon occur after five normal heartbeats and may induce tachycardia. It has been found that just as a pulse burst shortly after a rapid heartbeat can terminate tachycardia, it can also induce it if the heart was beating in normal sinus rhythm, especially if the burst is long. Once tachycardia is induced, the physician can observe the scanning; it begins with the lowest burst rate set in flip-flops D7–D10 (FIG. 3) because the programming itself automatically resets flip-flops 17–20 (FIGS. 5 and 6). The physician may then reprogram the pacer to have a tachy rate which is in the "normal" 130–225 beat-per-minute range, along with some selected new values for the lowest burst rate and other parameters whose combined efficacy is to be tested. By experimenting in this way, the physician can not only check the operation of the pacer, but he can also select optimum parameter values without the complications of invasive surgery.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A tachycardia control pacer comprising means for confirming tachycardia, means responsive to each operation of said confirming means for generating a burst of heart stimulating pulses at a constant rate, and means for controlling successive heart stimulating pulse bursts to be generated at different constant rates.

2. A tachycardia control pacer in accordance with claim 1 wherein the rate of the last burst which is successful in terminating tachycardia is retained, and further including means for governing the rate of the next burst following operation of said tachycardia confirming means to equal the retained rate.

3. A tachycardia control pacer in accordance with claim 2 wherein said generating means generates the same number of pulses during each pulse burst.

4. A tachycardia control pacer in accordance with claim 3 wherein said controlling means controls successive pulse bursts to have increasing rates, with the minimum pulse burst rate following the maximum pulse burst rate.

5. A tachycardia control pacer in accordance with claim 4 including means under external control for setting the minimum pulse burst rate.

6. A tachycardia control pacer in accordance with claim 3 further including means under external control for setting the number of pulses generated in each burst.

7. A tachycardia control pacer in accordance with claim 3 wherein said confirming means operates to confirm tachycardia responsive to a predetermined number of heartbeats occurring in succession, each of which occurs after the preceding heartbeat within a predetermined time period.

8. A tachycardia control pacer in accordance with claim 7 wherein said confirming means includes means to adjust said predetermined time period under external control such that heartbeats occurring at sinus rhythm result in tachycardia confirmation, said pulse generating means thereupon automatically operating in order to induce tachycardia.

9. A tachycardia control pacer in accordance with claim 3 wherein said generating means generates pulses with the time intervals between pulses in successive bursts differing by the same value.

10. A tachycardia control pacer in accordance with claim 3 further including means for detecting a normal heartbeat which occurs after a predetermined time interval which follows the preceding heartbeat to indicate tachycardia termination.

11. A tachycardia control pacer in accordance with claim 10 wherein said controlling means changes the value of burst rate following tachycardia confirmation, and further including means responsive to operation of said normal heartbeat detecting means for inhibiting any rate change by said controlling means during the cycle of operation which follows the next tachycardia confirmation.

12. A tachycardia control pacer in accordance with claim 3 wherein said tachycardia confirming means operates the same way whether the preceding heartbeats were in sinus rhythm or part of a tachycardia episode.

13. A tachycardia control pacer in accordance with claim 3 further including externally controlled means for programming said pulse generating means off.

14. A tachycardia control pacer in accordance with claim 3 further including means under external control for adjusting the range through which the pulse burst rates vary.

15. A tachycardia control pacer in accordance with claim 3 wherein said generating means controls the time interval between operation of said tachycardia confirming means and the first pulse in any ensuing burst to equal the time interval between any two pulses in the burst.

16. A tachycardia control pacer in accordance with claim 2 wherein said controlling means controls successive pulse bursts to have increasing rates, with the minimum pulse burst rate following the maximum pulse burst rate.

17. A tachycardia control pacer in accordance with claim 2 further including means under external control for setting the minimum pulse burst rate.

18. A tachycardia control pacer in accordance with claim 2 further including means under external control for setting the number of pulses generated in each burst.

19. A tachycardia control pacer in accordance with claim 2 wherein said confirming means operates to confirm tachycardia responsive to a predetermined number of heartbeats occurring in succession, each of which occurs after the preceding heartbeat within a predetermined time period.

20. A tachycardia control pacer in accordance with claim 19 wherein said confirming emans includes means to adjust said predetermined time period under external control such that heartbeats occurring at sinus rhythm result in tachycardia confirmation, said pulse generating means thereupon automatically operating in order to induce tachycardia.

21. A tachycardia control pacer in accordance with claim 2 wherein said generating means generates pulses with the time intervals between pulses in successive bursts differing by the same value.

22. A tachycardia control pacer in accordance with claim 2 further including means for detecting a normal heartbeat which occurs after a predetermined time interval which follows the preceding heartbeat to indicate tachycardia termination.

23. A tachycardia control pacer in accordance with claim 22 wherein said controlling means changes the value of burst rate following tachycardia confirmation, and further including means responsive to operation of said normal heartbeat detecting means for inhibiting any rate change by said controlling means during the cycle of operation which follows the next tachycardia confirmation.

24. A tachycardia control pacer in accordance with claim 2 wherein said tachycardia confirming means operates the same way whether the preceding heartbeats were in sinus rhythm or part of a tachycardia episode.

25. A tachycardia control pacer in accordance with claim 2 further including externally controlled means for programming said pulse generating means off.

26. A tachycardia control pacer in accordance with claim 2 further including means under external control for adjusting the range through which the pulse burst rates vary.

27. A tachycardia control pacer in accordance with claim 2 wherein said generating means controls the time interval between operation of said tachycardia confirming means and the first pulse in any ensuing burst to equal the time interval between any two pulses in the burst.

28. A tachycardia control pacer in accordance with claim 1 wherein said generating means generates the same number of pulses during each pulse burst.

29. A tachycardia control pacer in accordance with claim 1 wherein said controlling means controls successive pulse bursts to have increasing rates, with the minimum pulse burst rate following the maximum pulse burst rate.

30. A tachycardia control pacer in accordance with claim 1 further including means under external control for setting the minimum pulse burst rate.

31. A tachycardia control pacer in accordance with claim 1 further including means under external control for setting the number of pulses generated in each burst.

32. A tachycardia control pacer in accordance with claim 1 wherein said confirming means operates to confirm tachycardia responsive to a predetermined number of heartbeats occurring in succession, each of which occurs after the preceding heartbeat within a predetermined time period.

33. A tachycardia control pacer in accordance with claim 32 wherein said confirming means includes means to adjust said predetermined time period under external control such that heartbeats occurring at sinus rhythm result in tachycardia confirmation, said pulse generating means thereupon automatically operating in order to induce tachycardia.

34. A tachycardia control pacer in accordance with claim 1 wherein said generating means generates pulses with the time intervals between pulses in successive bursts differing by the same value.

35. A tachycardia control pacer in accordance with claim 1 further including means for detecting a normal heartbeat which occurs after a predetermined time interval which follows the preceding heartbeat to indicate tachycardia termination.

36. A tachycardia control pacer in accordance with claim 35 wherein said controlling means changes the value of burst rate following tachycardia confirmation, and further including means responsive to operation of said normal heartbeat detecting means for inhibiting any rate change by said controlling means during the cycle of operation which follows the next tachycardia confirmation.

37. A tachycardia control pacer in accordance with claim 1 wherein said tachycardia confirming means operates the same way whether the preceding heartbeats were in sinus rhythm or part of a tachycardia episode.

38. A tachycardia control pacer in accordance with claim 1 further including externally controlled means for programming said pulse generating means off.

39. A tachycardia control pacer in accordance with claim 1 further including means under external control for adjusting the range through which the pulse burst rates vary.

40. A tachycardia control pacer in accordance with claim 1 wherein said generating means controls the time interval between operation of said tachycardia confirming means and the first pulse in any ensuing burst to equal the time interval between any two pulses in the burst.

41. A tachycardia control pacer comprising means for confirming tachycardia, means responsive to said confirming means for generating a burst of at least three heart-stimulating pulses at a constant rate which potentially allows tachycardia to be terminated, means for scanning said rate during successive cycles of operation of said pulse burst generating means, means for detecting tachycardia termination, said pulse burst generating means ceasing to operate following tachycardia termination, and means for registering the last-used pulse rate which was successful in terminating tachycardia for first use in the next scan which follows tachycardia confirmation.

42. A tachycardia control pacer in accordance with claim 41 wherein said generating means generates the same number of pulses during each pulse burst.

43. A tachycardia control pacer in accordance with claim 41 wherein said scanning means causes successive pulse bursts to have increasing rates, with the minimum pulse burst rate following the maximum pulse burst rate.

44. A tachycardia control pacer in accordance with claim 41 further including means under external control for setting the minimum pulse burst rate.

45. A tachycardia control pacer in accordance with claim 41 further including means under external control for setting the number of pulses generated in each burst.

46. A tachycardia control pacer in accordance with claim 41 wherein said confirming means operates to confirm tachycardia responsive to a predetermined number of heartbeats occurring in succession, each of which occurs after the preceding heartbeat within a predetermined time period.

47. A tachycardia control pacer in accordance with claim 46 wherein said confirming means includes means to adjust said predetermined time period under external control such that heartbeats occurring at sinus rhythm result in tachycardia confirmation, said pulse generating means thereupon automatically operating in order to induce tachycardia.

48. A tachycardia control pacer in accordance with claim 41 wherein said scanning means causes the time intervals between pulses in successive bursts to differ by the same value.

49. A tachycardia control pacer in accordance with claim 41 further including means for detecting a normal heartbeat which occurs after a predetermined time interval which follows the preceding heartbeat to indicate tachycardia termination.

50. A tachycardia control pacer in accordance with claim 49 wherein said scanning means changes the value of burst rate following tachycardia confirmation, and further including means responsive to operation of said normal heartbeat detecting means for inhibiting any rate change by said controlling means during the cycle of operation which follows the next tachycardia confirmation.

51. A tachycardia control pacer in accordance with claim 41 wherein said tachycardia confirming means operates the same way whether the preceding heartbeats were in sinus rhythm or part of a tachycardia epidode.

52. A tachycardia control pacer in accordance with claim 41 further including externally controlled means for programming said pulse generating means off.

53. A tachycardia control pacer in accordance with claim 41 further including means under external control for adjusting the range through which the pulse burst rates vary.

54. A tachycardia control pacer in accordance with claim 41 wherein said generating means controls the time interval between operation of said tachycardia confirming means and the first pulse in any ensuing burst to equal the time interval between any two pulses in the burst.

* * * * *